US011255830B2

(12) United States Patent
Feinstein et al.

(10) Patent No.: US 11,255,830 B2
(45) Date of Patent: Feb. 22, 2022

(54) BIOSENSOR EXHIBITING SENSITIVITY TO TRINITROTOLUENE

(71) Applicant: Research Foundation of the City University of New York, New York, NY (US)

(72) Inventors: Paul Feinstein, New York, NY (US); Charlotte D'Hulst, Brooklyn, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 16/474,814

(22) PCT Filed: Jan. 2, 2018

(86) PCT No.: PCT/US2018/012117
§ 371 (c)(1),
(2) Date: Jun. 28, 2019

(87) PCT Pub. No.: WO2018/151875
PCT Pub. Date: Aug. 23, 2018

(65) Prior Publication Data

US 2019/0324004 A1 Oct. 24, 2019

Related U.S. Application Data

(60) Provisional application No. 62/440,773, filed on Dec. 30, 2016.

(51) Int. Cl.

| | |
|---|---|
| ***G01N 31/22*** | (2006.01) |
| ***A01K 67/027*** | (2006.01) |
| ***C12N 5/0793*** | (2010.01) |
| ***C12N 15/63*** | (2006.01) |
| ***G01N 33/50*** | (2006.01) |
| ***G01N 33/566*** | (2006.01) |

(52) U.S. Cl.
CPC ......... *G01N 31/22* (2013.01); *A01K 67/0278* (2013.01); *C12N 5/062* (2013.01); *C12N 15/63* (2013.01); *G01N 33/5058* (2013.01); *G01N 33/566* (2013.01); *A01K 2217/052* (2013.01); *A01K 2227/105* (2013.01); *A01K 2267/0393* (2013.01)

(58) Field of Classification Search
CPC ....... A01K 67/0278; A01K 2267/0393; G01N 33/5058
See application file for complete search history.

(56) References Cited

U.S. PATENT DOCUMENTS

| | | | |
|---|---|---|---|
| 7,223,550 | B2 | 5/2007 | Dhanasekaran et al. |
| 2010/0222561 | A1 | 9/2010 | Matsunami et al. |
| 2011/0177964 | A1 | 7/2011 | Broach et al. |
| 2015/0226755 | A1 | 8/2015 | Ai et al. |

FOREIGN PATENT DOCUMENTS

| | | |
|---|---|---|
| WO | WO 0017371 | 3/2000 |
| WO | WO 2014210585 | 12/2014 |
| WO | WO2017019179 | 2/2017 |
| WO | WO2017024028 | 2/2017 |

OTHER PUBLICATIONS

Harmar, A. J., Family-B G-protein-coupled receptors, Nov. 2001, Genome Biology 2(12):reviews 3013.1-3013.10 (Year: 2001).*

Li et al., A broadly tuned mouse odorant receptor that detects nitrotoluenes, Jun. 2012, J Neurochem. 121(6): 881-890 (Year: 2012).*

Tazir et al., The extremely broad odorant response profile of mouse olfactory sensory neurons expressing the odorant receptor MOR256-17 . . . , 2016, European Journal of Neuroscience, vol. 43, pp. 608-617, published online Dec. 15, 2015 @ https://doi.org/10.1111/ejn.13153l (Year: 2015).*

D'Hulst, C. et al.; MouSensor: A Versatile Genetic Platform to Create Super Sniffer Mice for Studying Human Odor Coding; Cell Reports; Jul. 26, 2016; pp. 1115-1125; vol. 16.

Bozza, T. et al.; Mapping of Class I and Class II Odorant Receptors to Glomerular Domains by Two Distinct Types of Olfactory Sensory Neurons in the Mouse; Neuron; Jan. 29, 2009; pp. 1-24; 61(2).

Fleischmann, A. et al.; Mice with a "Monoclonal" Nose: Perturbations in an Olfactory Map Impair Odor Discrimination; Neuron; Dec. 26, 2008; pp. 1-25; 60(6).

Vassalli, A. et al.; Minigenes Impart Odorant Receptor-Specific Axon Guidance in the Olfactory Bulb; Neuron; Aug. 15, 2002; pp. 681-696, vol. 35; Cell Press.

Vassalli, A. et al.; Homeodomain binding motifs modulate the probability of odorant receptor gene choice in transgenic mice; Mol Cell Neurosci.; Feb. 2011; pp. 1-30; 46(2).

Degl'innocenti, A. et al.; The Mouse Solitary Odorant Receptor Gene Promoters as Models for the Study of Odorant Receptor Gene Choice; PLOS ONE; Jan. 21, 2016; pp. 1-17; http://dx.doi.org/10.1371/journal.pone.0144698.

Rothman, A. et al.; The promoter of the mouse odorant receptor gene M71; Mol. Cell. Neurosci.; Jan. 8, 2005; pp. 535-546; vol. 28; Elsevier.

Saito, H. et al.; RTP Family Members Induce Functional Expression of Mammalian Odorant Receptors; Cell Nov. 24, 2004; pp. 679-691; vol. 119; Cell Press.

Nguyen, M. et al.; A Smell That Causes Seizure; PLOS One; Jul. 27, 2012; pp. 1-10; vol. 7; Issue 7; PLoS ONE.

Movahedi, K. et al.; Odorant receptors can mediate axonal identity and gene choice via cAMPindependent mechanisms; Open Biology; Jul. 2016; pp. 1-19; 6(7).

Fleischmann, A. et al.; Functional Interrogation of an Odorant Receptor Locus Reveals Multiple Axes of Transcriptional Regulation; PLOS; May 21, 2013; pp. 1-14; vol. 11, Issue 5.

(Continued)

*Primary Examiner* — Olga N Chernyshev

(74) *Attorney, Agent, or Firm* — Peter J. Mikesell; Schmeiser, Olsen & Watts, LLP

(57) ABSTRACT

A biosensor for detecting trinitrotoluene (TNT) is disclosed. The biosensor has cells, such as olfactory sensory neurons (or cilia derived therefrom), that preferentially express a TNT-responsive odorant receptor protein.

8 Claims, 7 Drawing Sheets

Specification includes a Sequence Listing.

(56) References Cited

OTHER PUBLICATIONS

Von Der Weid, B. et al.; Large-scale transcriptional profiling of chemosensory neurons identifies receptor-ligand pairs in vivo; Nature Neuroscience; Aug. 31, 2015; pp. 1-14; vol. 18.
Genbank; Mus musculus H-region enhancer sequence for "Negative feedback regulation ensures the one receptor-one olfactory neuron rule in mouse"; Jun. 28, 2005; Version: DQ086467.1 GI 68160280; 1 Page.
Serizawa, S. et al.; Negative Feedback Regulation Ensures the One Receptor-One Olfactory Neuron Rule in Mouse; Science; Dec. 19, 2003; pp. 2088-2094; vol. 302.
ISA/US; International Search Report/Written Opinion dated Oct. 31, 2016 in International Application PCT/US16/45338; 8 pages.
UNIPROTKB; Accession No. M0R6V4; Olfactory receptor 300; Apr. 3, 2013; https://www.uniprot.org/uniprot/M0R6V4.
ISA/US; International Search Report/Written Opinion dated Sep. 24, 2018 in International Application PCT/US18/12117; 18 pages.
Genbank, Olfactory receptor Olr319 [Rattus norvegicus]; Sep. 4, 2014; Version: NP_001000506.1; 2 Pages.
Radhika, V. et al.; Chemical sensing of DNT by engineered olfactory yeast strain; Nature Chemical Biology; May 7, 2007; pp. 325-330; vol. 3 No. 6.
Khan, M. et al; Regulation of the Probability of Mouse Odorant Receptor Gene Choice; Cell; Nov. 11, 2011; pp. 907-921; vol. 147.
Serizawa, S. et al.; One Neuron-one receptor rule in the mouse olfactory system; Trands in Genetics; Oct. 6, 2004; pp. 648-653; vol. 20, No. 12.
Feinstein, P. et al.; A contextual Model for Axonal Sorting into Glomeruli in the Mouse Olfactory System; Cell; May 11, 2004; pp. 817-831; vol. 117.
Sato, Y. et al.; Hierarchical Regulation of Odorant Receptor Fene Choice and Subsequent Axonal Projection of Olfactory Sensory Neurons in Zebrafish; The Journal of Neuroscience; Feb. 14, 2007; pp. 1606-1615; vol. 27, Issue 7.
Park, K. et al.; Role of stem cells in large animal genetic engineering in the TALENs-CRSPR era; Reproduction, Fertility and Development; 2014; pp. 65-73; vol. 26.
Prather, R. et al.; Genetically Engineered Pig Models for Human Diseases; Annu Rev Anim Biosci; Jan. 2013; 21 Pages; vol. 1.
Graham, D. et al.; Resources for the design of CRISPR gene editing experiments; Genome Biology; 2015; 21 pages.
Sieren, J. et al.; Development and translational imaging of a TP53 porcine tumorigenesis model; J. Clin Invest; Sep. 2014; pp. 4052-4066; vol. 124, No. 9.
Whitelaw, C. et al.; Engineering large animal models of human disease; Journal of Pathology; Nov. 28, 2015; pp. 247-256; vol. 238.
Leuchs, S. et al.; Inactivation and Iducible Oncogenic Mutation of p53in Gene Targeted Pigs; PLOS; Oct. 5, 2012; 8 pages; vol. 7, Issue 10.
Guri, G. et al.; Current Progress of Genetically Engineered Pig Models for Biomedical Research; BioResearch; Dec. 2014; pp. 255-264; vol. 3, No. 6.
Kuhlmann, K. et al.; The Membrane Proteome of Sensory Cilia to the Depth of Olfactory Receptors; Molecular & Cellular Proteomics; Apr. 18, 2014; pp. 1828-1843; 13.7.
Mayer, U. et al.; The proteome of rat olfactory sensory cilia; Proteomics; 2009; pp. 322-334; vol. 9.
Pfeuffer, E. et al.; Olfactory Adenylyl Cyclase; The Journal of Biological Chemistry; 1989; p. 18803-18807; vol. 264, No. 31.
Skylar, P. et al.; The Odorant-senstive Adenylate Cyclase of Olfactory Receptor Cells; The Journal of Biological Chemistry;1986; pp. 15538-15543; vol. 261, No. 33.

* cited by examiner

| OR | Fold change | P-Value |
|---|---|---|
| Olfr297 | 0.37 | 0.03 |
| Olfr597 | 0.43 | 0.06 |
| Olfr605 | 0.55 | 0.12 |
| Olfr566 | 0.4 | 0.30 |

SEQUENCE LISTING

```
<160> NUMBER OF SEQ ID NOS: 35

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA fragment for enhancing expression
      of a nearby odorant receptor coding sequence.

<400> SEQUENCE: 1

acataacttt ttaatgagtc t                                               21


<210> SEQ ID NO 2
<211> LENGTH: 314
<212> TYPE: PRT
<213> ORGANISM: Rattus norvegicus

<400> SEQUENCE: 2

Met Gly Glu Asn Asn Asn Val Thr Glu Phe Val Leu Leu Gly Leu Thr
1               5                   10                  15

Gln Asp Pro Thr Gly Gln Lys Ala Leu Phe Val Met Phe Leu Leu Met
            20                  25                  30

Tyr Ile Val Thr Ile Val Gly Asn Leu Leu Ile Val Gly Thr Val Ile
        35                  40                  45

Ala Ser Pro Ser Leu Asn Ser Pro Met Tyr Phe Phe Leu Ala Phe Leu
    50                  55                  60

Ser Leu Met Asp Ala Val Tyr Ser Thr Ala Ile Leu Pro Lys Leu Leu
65                  70                  75                  80

Lys Asp Leu Val Cys Asp Lys Lys Thr Ile Ser Phe Thr Ala Cys Leu
                85                  90                  95

Val Gln Leu Phe Val Glu His Leu Phe Gly Gly Ala Glu Val Phe Leu
            100                 105                 110

Leu Val Val Met Ala Tyr Asp Arg Tyr Val Ala Ile Cys Lys Pro Leu
        115                 120                 125

His Tyr Leu Thr Thr Met Asn Gln Gln Val Cys Ile Ser Leu Leu Val
    130                 135                 140

Val Ala Trp Val Gly Gly Phe Ala His Ala Leu Val Gln Val Leu Ser
145                 150                 155                 160
```

-continued

Val Tyr Lys Leu Pro Phe Cys Gly Pro Asn Val Ile Asp His Phe Gly
165 170 175

Cys Asp Met Tyr Pro Leu Leu Ala Leu Val Cys Thr Asp Thr Tyr Phe
180 185 190

Ile Gly Leu Thr Val Val Ala Asn Asn Gly Ala Met Cys Met Ile Val
195 200 205

Phe Val Leu Leu Leu Phe Ser Tyr Gly Ile Ile Leu Ser Ser Leu Lys
210 215 220

Thr His Ser Gln Glu Gly Arg Arg Lys Ala Leu Ser Thr Cys Ser Ser
225 230 235 240

His Ile Met Val Val Val Leu Phe Phe Val Pro Cys Ile Phe Met Tyr
245 250 255

Val Arg Pro Val Ser Asn Phe Pro Ile Asp Lys Ser Ile Ser Val Phe
260 265 270

Tyr Thr Ala Ile Thr Pro Met Leu Asn Pro Leu Ile Tyr Thr Leu Arg
275 280 285

Asn Ser Glu Ile Lys Asn Ser Met Gly Lys Leu Trp Tyr Lys Met Ile
290 295 300

Ser Ile Gly Arg Val Arg Ile Phe Ala Cys
305 310

<210> SEQ ID NO 3
<211> LENGTH: 307
<212> TYPE: PRT
<213> ORGANISM: Rattus norvegicus

<400> SEQUENCE: 3

Met Ala Pro Ile Asn Gln Ser Val Val Thr Met Phe Phe Leu Gln Asn
1 5 10 15

Phe Val Asp Asp Pro Trp Ile Gln Asn Val Leu Phe Cys Phe Phe Phe
20 25 30

Ala Leu Phe Val Ala Ala Ile Ala Gly Asn Gly Leu Ile Ile Thr Val
35 40 45

Ile His Ser Ser Ala Asn Leu His Thr Pro Met Tyr Phe Phe Leu Val
50 55 60

Asn Leu Ser Leu Met Asp Val Ile Cys Thr Val Thr Val Leu Pro Lys
65 70 75 80

Val Leu Gln Ser Leu Val Ala Glu Asn Ala Ile Ser Tyr Gly Gly Cys
85 90 95

Leu Thr Gln Met Phe Val Phe Ser Trp Val Leu Gly Ser Glu Leu Leu
100 105 110

Leu Phe Ser Ala Met Ala Tyr Asp Arg Tyr Leu Ala Ile Cys Arg Pro
115 120 125

Leu His Tyr Gly Thr Leu Met Ser Gly Arg Val Cys Ile Ala Leu Ala
130 135 140

Thr Phe Val Trp Phe Thr Gly Ala Leu Asn Ser Leu Val Leu Thr Cys
145 150 155 160

Leu Val Leu Pro Leu Ser Phe Cys Gly Pro Asn Leu Ile Thr His Phe
165 170 175

Phe Cys Glu Ile Pro Ser Val Leu Met Leu Ser Cys Ser Pro Thr Phe
180 185 190

Ile Asn Asp Ile Met Thr Val Ile Ala Asp Met Phe Leu Thr Gly Leu
195 200 205

Asn Phe Leu Leu Thr Met Thr Ser Tyr Gly Phe Ile Ile Ala Ser Ile

-continued

```
    210                 215                 220

Leu Arg Ile Arg Ser Ala Glu Gly Lys Lys Arg Ala Phe Ser Thr Cys
225                 230                 235                 240

Ser Ala His Leu Val Val Val Thr Leu Tyr Tyr Ser Thr Val Leu Tyr
                245                 250                 255

Thr Tyr Val Arg Pro Ala Leu Gly Thr Ser Gly Leu Leu Asp Lys Val
            260                 265                 270

Ile Ala Val Leu Tyr Thr Thr Val Thr Pro Ser Leu Asn Pro Leu Ile
        275                 280                 285

Tyr Thr Leu Arg Asn Lys Glu Phe Lys Thr Ser Phe Lys Lys Leu Leu
    290                 295                 300

Phe Pro Asn
305


<210> SEQ ID NO 4
<211> LENGTH: 309
<212> TYPE: PRT
<213> ORGANISM: Rattus norvegicus

<400> SEQUENCE: 4

Met Glu Thr Ile Asn Lys Thr Ala Lys Ile Asn Phe Phe Phe Arg Pro
1               5                   10                  15

Phe Ser Ser Asp Pro Gly Val Gln Met Val Ile Phe Val Thr Phe Leu
            20                  25                  30

Val Met Tyr Leu Thr Ser Leu Ser Gly Asn Ala Thr Ile Ala Val Ile
        35                  40                  45

Val His Ile Asn His Ala Leu His Thr Pro Met Tyr Phe Phe Leu Ala
    50                  55                  60

Asn Leu Ala Val Leu Glu Ile Phe Tyr Thr Ser Ser Ile Ala Pro Leu
65                  70                  75                  80

Ala Leu Ala Asn Leu Leu Ser Met Gly Lys Thr Pro Val Ser Ile Thr
                85                  90                  95

Gly Cys Gly Thr Gln Met Phe Phe Phe Val Phe Leu Gly Gly Ala Asp
            100                 105                 110

Cys Val Leu Leu Ala Val Met Ala Tyr Asp Arg Phe Val Ala Ile Cys
        115                 120                 125

Tyr Pro Leu Arg Tyr Thr Leu Ile Met Ser Trp Ser Leu Cys Val Glu
    130                 135                 140

Met Met Val Gly Ser Leu Val Leu Gly Cys Leu Leu Ser Leu Pro Leu
145                 150                 155                 160

Thr Ile Leu Ile Phe His Leu Pro Phe Cys His Asn Asn Glu Ile Tyr
                165                 170                 175

His Phe Tyr Cys Asp Met Pro Ala Val Ile Arg Leu Ala Cys Gly Asp
            180                 185                 190

Thr His Val His Arg Thr Ala Leu Tyr Ile Ile Ser Phe Ile Val Leu
        195                 200                 205

Ser Ile Pro Leu Thr Leu Ile Ser Ile Ser Tyr Val Phe Ile Ile Thr
    210                 215                 220

Ala Ile Leu Arg Ile Arg Ser Ala Glu Gly Arg His Arg Ala Phe Ser
225                 230                 235                 240

Thr Cys Ser Ser His Ile Val Val Val Leu Leu Gln Tyr Gly Cys Thr
                245                 250                 255

Ser Phe Ile Tyr Leu Ser Pro Ser Ser Ser Tyr Ser Pro Glu Met Gly
            260                 265                 270
```

Arg Met Val Ser Val Val Tyr Thr Phe Ile Thr Pro Ile Leu Asn Pro
        275                 280                 285

Leu Ile Tyr Ser Met Arg Asn Lys Glu Leu Lys Asp Ala Leu Arg Lys
    290                 295                 300

Ala Leu Lys Lys Phe
305

<210> SEQ ID NO 5
<211> LENGTH: 310
<212> TYPE: PRT
<213> ORGANISM: Mus musculus

<400> SEQUENCE: 5

Met Met Asn Ser Thr Met Val Thr Glu Phe Leu Leu Glu Val Phe Ala
1               5                   10                  15

Glu Thr Trp Glu Leu Arg Val Leu Leu Ser Val Leu Phe Leu Leu Val
            20                  25                  30

Tyr Leu Gly Ser Leu Phe Gly Asn Leu Thr Ile Ile Ile Val Thr Thr
        35                  40                  45

Val Asp Gln Thr Leu Asn Thr Pro Met Tyr Phe Phe Leu Arg Asn Leu
    50                  55                  60

Ser Ile Leu Asp Met Cys Tyr Val Ser Ile Thr Val Pro Asn Ala Cys
65                  70                  75                  80

Ile Asn Ser Leu Thr Asp His Arg Asn Ile Ser Val Thr Gly Cys Ala
                85                  90                  95

Ala Gln Ile Phe Leu Phe Phe Phe Cys Ala Cys Val Glu Val Gln Phe
            100                 105                 110

Leu Thr Ile Met Ala Gln Asp Arg Tyr Val Ala Ile Cys Lys Pro Leu
        115                 120                 125

Leu Tyr Pro Met Ile Met Asn His Gln Phe Cys Val Gln Met Thr Leu
    130                 135                 140

Ala Ser Leu Leu Thr Ser Leu Ile Leu Ser Gly Met Asn Thr Phe Lys
145                 150                 155                 160

Thr Phe Gln Leu Ser Phe Cys His Ser Asn Val Val Pro Gln Phe Phe
                165                 170                 175

Cys Glu Leu Pro Ala Leu Leu Arg Leu Thr Cys Ser Asp Thr Phe Asn
            180                 185                 190

Asn Lys Ile Ile Leu Leu Leu Thr Ala Ile Gly Leu Ser Gly Thr Cys
        195                 200                 205

Phe Thr Phe Ile Ala Ile Ser Tyr Val His Ile Leu Ser Thr Val Leu
    210                 215                 220

Lys Val Pro Val Lys Gly Glu Arg Gly Lys Ala Phe Ser Thr Cys Val
225                 230                 235                 240

Pro His Ile Ile Val Ala Tyr Leu Phe Leu Cys Ser Gly Ala Tyr Ala
                245                 250                 255

Tyr Leu Arg Pro Pro Ala Ile Ser Glu Val Val Glu Asp Met Thr Leu
            260                 265                 270

Ser Val Phe Tyr Thr Thr Val Pro Pro Phe Leu Asn Pro Ile Ile Tyr
        275                 280                 285

Ser Leu Arg Asn Lys Gln Ile Lys Lys Ala Val Lys Lys Val Ile Phe
    290                 295                 300

Arg Phe Phe Ile Val Glu
305                 310

<210> SEQ ID NO 6

-continued

<211> LENGTH: 259
<212> TYPE: PRT
<213> ORGANISM: Rattus norvegicus

<400> SEQUENCE: 6

Met Glu Val Arg Asn Val Thr Glu Phe Val Leu Leu Gly Leu Thr Ser
1 5 10 15

Asn Pro Arg Ser Gln Val Val Leu Phe Val Leu Phe Leu Val Ile Tyr
20 25 30

Leu Leu Thr Leu Val Gly Asn Leu Leu Met Leu Met Leu Ile Ser Ser
35 40 45

Asp Ala His Leu Arg Thr Pro Met Tyr Phe Phe Leu Arg Tyr Leu Ser
50 55 60

Phe Met Asp Ala Phe Tyr Ser Ser Val Ile Val Pro Lys Leu Leu Arg
65 70 75 80

Asn Leu Ile Ser Glu Trp Lys Thr Ile Ser Phe Leu Gly Cys Phe Ile
85 90 95

Gln Ile Ala Leu Val Ile Phe Ser Gly Ala Thr Glu Ala Cys Leu Leu
100 105 110

Ser Ala Met Ala Tyr Asp Arg Phe Gln Ala Val Cys His Pro Leu Leu
115 120 125

Tyr Val Val Thr Met Asn Gly Lys Val Cys Ser Gly Met Val Ala Ile
130 135 140

Ser Trp Ala Val Gly Met Ser Val Ser Leu Val Asn Thr Leu Leu Leu
145 150 155 160

Ala Gln Glu Asn Phe Cys Gly Pro Asn Val Ile His Asn Phe Ala Cys
165 170 175

Glu Leu Pro Pro Val Leu Leu Leu Val Cys Ser Asn Pro His Thr Thr
180 185 190

Ile Ala Ser Ile Leu Thr Thr Leu Val Ile Leu Gly Phe Gly Ser Leu
195 200 205

Ile Leu Leu Leu Gly Ser Tyr Ser Arg Ile Ile Lys Thr Ala Leu Gly
210 215 220

Val Asn Ser Ala Thr Gly Arg Ser Lys Ile Phe Ser Thr Cys Ser Ser
225 230 235 240

His Phe Leu Val Val Thr Ile Phe Tyr Gly Ser Gly Val Phe Arg Cys
245 250 255

Val Thr Arg

<210> SEQ ID NO 7
<211> LENGTH: 314
<212> TYPE: PRT
<213> ORGANISM: Rattus norvegicus

<400> SEQUENCE: 7

Met Glu Glu Thr Asn Asn Val Thr Glu Phe Ile Leu Leu Gly Leu Thr
1 5 10 15

Gln Asp Pro Ala Gly Gln Lys Val Leu Phe Val Met Phe Leu Leu Ile
20 25 30

Tyr Ile Val Thr Ile Gly Gly Asn Leu Leu Ile Val Gly Thr Val Ile
35 40 45

Ala Ser Pro Ser Leu Gly Ser Pro Met Tyr Phe Phe Leu Ala Phe Leu
50 55 60

Ser Leu Met Asp Ala Val Tyr Ser Thr Ala Ile Leu Pro Lys Leu Leu
65 70 75 80

-continued

Thr Asp Leu Leu Cys Asp Lys Lys Ala Ile Ser Val Lys Ala Cys Leu
85 90 95

Val Gln Leu Phe Val Glu His Leu Phe Gly Gly Ser Glu Val Phe Ile
100 105 110

Leu Val Val Met Ala Tyr Asp Arg Tyr Val Ala Ile Cys Lys Pro Leu
115 120 125

His Tyr Leu Thr Ile Met Asn Arg Gln Val Cys Ile Leu Leu Leu Val
130 135 140

Val Ser Trp Ala Gly Gly Phe Ala His Ala Leu Leu Gln Val Ile Ser
145 150 155 160

Val Tyr Leu Leu Pro Phe Cys Gly Pro Asn Val Ile Asp His Phe Ala
165 170 175

Cys Asp Met Tyr Pro Leu Leu Gly Leu Ala Cys Thr Asp Thr Tyr Phe
180 185 190

Leu Gly Leu Ser Val Ile Gly Asn Asn Gly Ala Met Ser Ile Val Val
195 200 205

Phe Ile Leu Leu Leu Val Ser Tyr Gly Ile Ile Leu Asn Ser Leu Lys
210 215 220

Thr Tyr Ser Gln Glu Gly Arg Arg Lys Ala Leu Ser Thr Cys Ser Ser
225 230 235 240

His Ile Met Val Val Ile Leu Phe Phe Val Pro Cys Ile Phe Met Tyr
245 250 255

Val Arg Pro Val Ser Asn Phe Pro Ile Asp Lys Tyr Ile Thr Val Phe
260 265 270

Tyr Thr Ile Phe Thr Pro Met Leu Asn Pro Leu Ile Tyr Thr Leu Arg
275 280 285

Asn Met Glu Ile Lys Asn Cys Met Ala Lys Leu Trp Gly Lys Met Phe
290 295 300

Thr Lys Asp Ile Lys Lys Ile Ser Ala His
305 310

<210> SEQ ID NO 8
<211> LENGTH: 317
<212> TYPE: PRT
<213> ORGANISM: Rattus norvegicus

<400> SEQUENCE: 8

Met Ala Ile Gly Asn Gln Thr Arg Val Thr Glu Phe Ile Leu Met Ser
1 5 10 15

Phe Ser Ser Leu Pro Thr Glu Ile Gln Thr Leu Leu Phe Leu Ala Phe
20 25 30

Leu Ser Ile Tyr Leu Val Thr Leu Leu Gly Asn Ser Leu Ile Ile Leu
35 40 45

Val Thr Leu Ala Asp Pro Met Leu Gln Ser Pro Met Tyr Phe Leu Leu
50 55 60

Arg Asn Leu Ala Phe Leu Glu Ile Gly Phe Asn Leu Val Ile Val Pro
65 70 75 80

Lys Met Leu Gly Thr Leu Ile Ala Gln Asp Thr Ser Ile Ser Phe Leu
85 90 95

Gly Cys Ala Thr Gln Met Tyr Phe Phe Phe Phe Phe Gly Val Ala Glu
100 105 110

Cys Phe Leu Leu Ala Thr Met Ala Tyr Asp Arg Tyr Val Ala Ile Cys
115 120 125

Ser Pro Leu His Tyr Pro Val Ile Met Asn Gln Gly Thr Arg Ala Arg
130 135 140

-continued

```
Leu Ala Ala Ala Ser Trp Phe Pro Gly Phe Pro Val Ala Thr Val Gln
145                 150                 155                 160

Thr Thr Trp Leu Phe Ser Phe Pro Phe Cys Ala Asn Asn Lys Val Asn
                165                 170                 175

His Phe Phe Cys Asp Ser Pro Pro Val Leu Arg Leu Val Cys Ala Asp
            180                 185                 190

Thr Ala Arg Phe Glu Val Tyr Ala Ile Val Gly Thr Ile Leu Val Val
        195                 200                 205

Met Ile Pro Cys Leu Leu Ile Leu Cys Ser Tyr Thr Leu Ile Val Ala
    210                 215                 220

Ser Ile Leu Lys Ile Pro Ser Ala Gln Gly Lys His Lys Ala Phe Ser
225                 230                 235                 240

Thr Cys Ser Ser His Leu Leu Val Val Ser Leu Phe Tyr Val Ser Ser
                245                 250                 255

Ser Leu Thr Tyr Phe Arg Pro Lys Ser Asn Asn Ser Pro Glu Ser Lys
            260                 265                 270

Lys Leu Leu Ser Leu Ser Tyr Thr Val Val Thr Pro Met Leu Asn Pro
        275                 280                 285

Ile Ile Tyr Ser Leu Arg Asn Asn Glu Val Lys Asn Ala Leu Ser Arg
    290                 295                 300

Thr Phe Tyr Lys Ala Leu Ala Leu Arg Asn His Ile Thr
305                 310                 315


<210> SEQ ID NO 9
<211> LENGTH: 316
<212> TYPE: PRT
<213> ORGANISM: Rattus norvegicus

<400> SEQUENCE: 9

Met Asn Leu Gly Asn Glu Ser Ala Pro Lys Ile Phe Ile Leu Leu Gly
1               5                   10                  15

Phe Ser Asn Tyr Pro Trp Leu Glu Met Pro Leu Phe Ile Met Val Leu
            20                  25                  30

Val Ala Tyr Val Cys Thr Val Val Gly Asn Ile Ser Ile Ile Val Val
        35                  40                  45

Ser Lys Ile Asp Pro Gln Leu Asp Ser Pro Met Tyr Phe Phe Leu Ser
    50                  55                  60

Asn Leu Ser Phe Leu Asp Leu Cys Phe Thr Thr Thr Thr Ile Pro Gln
65                  70                  75                  80

Leu Leu Arg Asn Leu Trp Gly Pro Asp Lys Ser Ile Ser Tyr Arg Gly
                85                  90                  95

Cys Val Thr Gln Phe Tyr Ile Phe His Phe Leu Gly Ala Thr Glu Cys
            100                 105                 110

Ile Leu Leu Ala Val Met Ser Leu Asp Arg Tyr Ile Ala Ile Cys Lys
        115                 120                 125

Pro Leu Arg Tyr Pro Ala Ile Met His Gln Gln Phe Cys Ile Leu Leu
    130                 135                 140

Met Phe Met Thr Trp Leu Ser Gly Leu Ala Asn Ser Leu Leu Gln Ser
145                 150                 155                 160

Thr Leu Thr Val Lys Leu Pro Phe Cys Gly Asn Asn Lys Val Asp Asn
                165                 170                 175

Phe Leu Cys Glu Val Pro Val Met Ile Lys Met Ser Cys Ala Asn Thr
            180                 185                 190

Ala Phe Asn Ile Ala Met Leu Ser Ile Val Gly Thr Phe Tyr Ser Leu
```

-continued

```
        195                 200                 205

Val Pro Leu Ser Leu Ile Leu Val Ser Tyr Gly Phe Ile Val Ala Thr
    210                 215                 220

Val Leu Arg Ile Arg Ser Ser Glu Gly Lys Lys Lys Ala Phe Asn Thr
225                 230                 235                 240

Cys Gly Ser His Val Val Val Val Thr Leu Phe Tyr Gly Pro Val Ile
                245                 250                 255

Ser Met Tyr Val Gln Pro Ser Ser Ser Ser Ser Gln Asp Lys Asn Lys
            260                 265                 270

Leu Leu Ser Leu Phe Tyr Ser Leu Val Thr Pro Met Leu Asn Pro Phe
        275                 280                 285

Ile Tyr Thr Leu Arg Asn Lys Asp Val Lys Gly Ala Met Arg Arg Phe
    290                 295                 300

Leu Val Ser Leu Phe His Lys Glu Ser Glu Gln Thr
305                 310                 315


<210> SEQ ID NO 10
<211> LENGTH: 312
<212> TYPE: PRT
<213> ORGANISM: Rattus norvegicus

<400> SEQUENCE: 10

Met Asn Gly Gly Asn Gln Ser Glu Leu Ser Glu Phe Val Leu Leu Gly
1               5                   10                  15

Leu Phe Arg Ser Gln Asn Leu Gln Val Val Leu Phe Val Ile Phe Leu
            20                  25                  30

Ile Phe Tyr Leu Leu Ile Val Ser Gly Asn Ile Val Ile Met Phe Leu
        35                  40                  45

Ile Thr Ile Asp Arg His Leu His Ser Pro Met Tyr Phe Leu Leu Ala
    50                  55                  60

Asn Leu Ser Phe Val Asp Ile Trp Leu Ser Ser Val Thr Thr Pro Lys
65                  70                  75                  80

Met Ile Thr Asp Phe Leu Arg Glu His Lys Thr Ile Ser Phe Ala Gly
                85                  90                  95

Cys Met Ser Gln Val Phe Phe Ala His Cys Ile Ala Ala Gly Glu Met
            100                 105                 110

Val Leu Leu Leu Val Met Ala Tyr Asp Arg Tyr Val Ala Ile Cys Lys
        115                 120                 125

Pro Leu His Tyr Phe Thr Ile Met Asn Leu Arg Arg Cys Thr Gly Leu
    130                 135                 140

Val Leu Thr Ser Trp Thr Val Gly Phe Val His Ala Leu Ser Gln Leu
145                 150                 155                 160

Val Ala Val Leu Gln Leu Pro Leu Cys Gly Pro Leu Glu Ile Asp Ser
                165                 170                 175

Phe Phe Cys Asp Met Pro Leu Val Ile Lys Leu Ala Cys Ile Asp Ser
            180                 185                 190

His Asp Leu Asp Met Leu Met Asn Ala Asp Cys Gly Ile Val Val Val
        195                 200                 205

Ser Cys Phe Ile Leu Leu Leu Ile Ser Tyr Thr Tyr Ile Leu Val Thr
    210                 215                 220

Val His Arg Ser Ala Lys Ala Gly Ala Ser Lys Ala Leu Ser Thr Cys
225                 230                 235                 240

Thr Ala His Ile Thr Val Val Met Leu Leu Phe Leu Pro Cys Ile Phe
                245                 250                 255
```

-continued

```
Ile Tyr Val Trp Pro Leu Asn Ile Thr Trp Leu Asp Lys Phe Leu Ala
            260                 265                 270

Val Phe Tyr Ser Val Val Thr Pro Leu Leu Asn Pro Ala Ile Tyr Thr
        275                 280                 285

Leu Arg Asn Lys Glu Ile Lys Asn Ala Leu Lys Arg Phe Lys Ser Tyr
    290                 295                 300

Val Ile Asn His Lys Val Asn Thr
305                 310


<210> SEQ ID NO 11
<211> LENGTH: 312
<212> TYPE: PRT
<213> ORGANISM: Rattus norvegicus

<400> SEQUENCE: 11

Met Ile Lys Gly Lys Asn Ile Thr Glu Ile Thr Gln Phe Ile Leu Leu
1               5                   10                  15

Gly Phe Ser Asp Phe Pro Gln Ile Thr Ala Leu Leu Phe Val Ile Phe
            20                  25                  30

Leu Thr Leu Tyr Ile Thr Ala Leu Thr Trp Asn Leu Ser Leu Ile Val
        35                  40                  45

Leu Ile Arg Met Asp Ser Tyr Leu His Thr Pro Met Tyr Phe Phe Leu
    50                  55                  60

Ser Asn Leu Ala Phe Ile Asp Leu Cys Tyr Ile Thr Ser Thr Val Pro
65                  70                  75                  80

Lys Met Leu Ser Asn Phe Phe Gln Glu Lys Gln Thr Ile Ser Phe Val
                85                  90                  95

Asp Cys Ile Val Gln Tyr Phe Ile Leu Ser Thr Met Gly Leu Thr Glu
            100                 105                 110

Ser Cys Leu Met Thr Val Met Ala Tyr Asp Arg Tyr Ala Ala Ile Cys
        115                 120                 125

Asn Pro Leu Leu Tyr Ser Ser Ile Met Ser Pro Ser Leu Cys Ala Arg
    130                 135                 140

Met Leu Leu Gly Ser Tyr Ala Ala Gly Leu Val Gly Ser Val Ser Gln
145                 150                 155                 160

Val Cys Ala Leu Leu Gln Leu His Phe Cys Gly Ser Asn Val Ile Arg
                165                 170                 175

His Phe Phe Cys Asp Met Pro Gln Leu Leu Asn Leu Ser Cys Ile Asp
            180                 185                 190

Thr Leu Phe Ala Gln Ile Leu Leu Ala Val Leu Thr Thr Leu Phe Gly
        195                 200                 205

Phe Ser Asn Ala Leu Ala Ile Met Ile Ser Tyr Gly His Ile Ile Leu
    210                 215                 220

Ser Ile Met Lys Ile Thr Ser Val Lys Gly Arg Ser Lys Ser Phe Asn
225                 230                 235                 240

Thr Cys Ala Ser His Val Thr Ala Val Ser Leu Phe Tyr Thr Ser Ser
                245                 250                 255

Val Phe Val Tyr Leu Ser Ser Ser Ser Gly Gly Ser Ser Ser Phe Asp
            260                 265                 270

Arg Phe Ala Ser Val Phe Tyr Asn Val Met Ile Pro Met Leu Asn Pro
        275                 280                 285

Leu Val Tyr Ser Leu Arg Asn Lys Glu Ile Arg Asp Ala Val Lys Arg
    290                 295                 300

Leu Lys Lys Lys Leu Gly Cys Cys
305                 310
```

<210> SEQ ID NO 12
<211> LENGTH: 311
<212> TYPE: PRT
<213> ORGANISM: Rattus norvegicus

<400> SEQUENCE: 12

```
Met Gln Asn Gln Ser Phe Val Asn Glu Phe Ile Leu Leu Gly Leu Ser
1               5                   10                  15

Gln Asn Pro Lys Val Glu Lys Ile Leu Phe Val Val Phe Leu Leu Val
            20                  25                  30

Tyr Ile Ala Thr Ile Gly Gly Asn Ile Met Ile Val Val Thr Ile Ile
        35                  40                  45

Tyr Ser Pro Ala Leu Leu Gly Ser Pro Met Tyr Phe Phe Leu Ile Phe
    50                  55                  60

Leu Ser Leu Leu Asp Ala Cys Thr Ser Ser Thr Val Thr Pro Lys Met
65                  70                  75                  80

Ile Val Asp Phe Phe Tyr Glu Arg Lys Thr Ile Ser Phe Glu Cys Cys
                85                  90                  95

Ile Thr Gln Leu Phe Thr Ser His Phe Phe Ala Gly Val Glu Val Ile
            100                 105                 110

Ile Leu Thr Ser Met Ala Tyr Asp Arg Tyr Val Ala Ile Cys Lys Pro
        115                 120                 125

Leu His Tyr Ser Ser Ile Met Thr Arg Arg Leu Cys Gly Thr Leu Val
    130                 135                 140

Gly Val Ala Trp Thr Gly Gly Phe Leu His Ser Ile Thr Gln Val Ile
145                 150                 155                 160

Phe Thr Leu Gln Leu Pro Phe Cys Gly Pro Asn Phe Ile Asp His Phe
                165                 170                 175

Ile Cys Asp Leu Phe Pro Leu Leu Gln Leu Ala Cys Thr Asp Thr His
            180                 185                 190

Ile Phe Val Ile Leu Val Phe Ala Asn Ser Gly Ser Phe Cys Ile Ile
        195                 200                 205

Ile Phe Ser Leu Leu Ile Ile Ser Tyr Gly Val Ile Leu Phe Ser Leu
    210                 215                 220

Arg Gly His Ser Ser Glu Gly Arg Arg Lys Ala Leu Ser Thr Cys Gly
225                 230                 235                 240

Ser His Ile Thr Val Met Ile Leu Phe Phe Val Pro Cys Met Leu Ile
                245                 250                 255

Tyr Ala Arg Pro Ser Ser Ala Phe Ser Phe Glu Lys Asn Thr Leu Ile
            260                 265                 270

Phe Ala Ser Val Leu Thr Pro Leu Leu Asn Pro Met Val Tyr Thr Phe
        275                 280                 285

Arg Asn Lys Glu Met Lys Asn Ala Ile Arg Lys Met Ser Arg Lys Leu
    290                 295                 300

Ile Val Val Ser Asn Thr Phe
305                 310
```

<210> SEQ ID NO 13
<211> LENGTH: 264
<212> TYPE: PRT
<213> ORGANISM: Rattus norvegicus

<400> SEQUENCE: 13

```
Met Gly Gly Val Asn Gln Thr Thr Ile Ser Glu Phe Ile Leu Leu Gly
1               5                   10                  15
```

```
Leu Ser Asp Asp Pro Ala Leu Gln Pro Phe Ile Phe Thr Leu Phe Leu
            20                  25                  30

Ser Ile Tyr Leu Ile Thr Thr Leu Gly Asn Leu Leu Ile Ile Leu Ala
        35                  40                  45

Val Ser Phe Asp Ser Gln Leu His Thr Pro Met Tyr Phe Phe Leu Ser
    50                  55                  60

Asn Leu Ser Phe Asn Asp Ile Cys Ile Ile Thr Thr Thr Ile Pro Lys
65                  70                  75                  80

Met Leu Met Asn Val Gln Ser His Asp Gln Ser Ile Thr Tyr Lys Gly
                85                  90                  95

Cys Leu Ser Gln Val Tyr Leu Ile Val Asn Phe Gly Ser Ile Glu Ser
            100                 105                 110

Cys Leu Leu Ala Val Met Ala Tyr Asp Arg Tyr Val Ala Ile Cys His
        115                 120                 125

Pro Leu Lys Tyr Thr Val Ile Met Asn His Tyr Phe Cys Val Met Leu
    130                 135                 140

Leu Leu Phe Ser Val Phe Val Ser Ile Ala His Ala Leu Phe His Ile
145                 150                 155                 160

Leu Met Val Leu Ile Leu Thr Phe Cys Thr Lys Thr Glu Ile Pro His
                165                 170                 175

Phe Phe Cys Glu Leu Ala His Ile Ile Lys Leu Thr Cys Ser Asp Asn
            180                 185                 190

Phe Ile Asn Tyr Leu Leu Ile Tyr Thr Val Ser Val Leu Phe Phe Gly
        195                 200                 205

Val His Ile Val Gly Ile Ile Leu Ser Tyr Ile Tyr Thr Val Ser Ser
    210                 215                 220

Val Leu Arg Met Ser Leu Leu Gly Gly Met Tyr Lys Ala Phe Ser Thr
225                 230                 235                 240

Cys Gly Ser His Leu Ser Val Val Ser Val Leu Trp His Arg Phe Trp
                245                 250                 255

Gly Thr His Lys Leu Ser Thr Tyr
            260


<210> SEQ ID NO 14
<211> LENGTH: 253
<212> TYPE: PRT
<213> ORGANISM: Rattus norvegicus

<400> SEQUENCE: 14

Met Phe Gly Asn Gly Ala Ile Met Met Ile Val Ser Leu Asp Pro Arg
1               5                   10                  15

Leu His Ser Pro Met Tyr Phe Phe Leu Gly Asn Leu Ala Cys Leu Asp
            20                  25                  30

Ile Ser Phe Ser Thr Val Thr Val Pro Lys Met Leu Glu Asn Phe Ser
        35                  40                  45

Ile Ser Lys Ala Ile Ser Phe Leu Gly Cys Ile Thr Gln Leu Tyr Phe
    50                  55                  60

Phe His Phe Leu Gly Ser Thr Glu Ala Leu Leu Leu Thr Ile Met Ala
65                  70                  75                  80

Phe Asp His Phe Val Ala Ile Cys Arg Pro Leu His Tyr Pro Ser Ile
                85                  90                  95

Met Asn His Gln Val Cys Ile Gln Arg Ala Val Phe Ile Trp Ala Thr
            100                 105                 110

Pro Phe Leu His Ala Leu Val His Ser Arg Leu Thr Ser Arg Leu Asn
```

-continued

```
        115                 120                 125

Phe Cys Ser Ser Asn Asn Val His His Phe Phe Cys Asp Val Lys Pro
    130                 135                 140

Leu Leu Glu Leu Ala Cys Gly Asn Thr Glu Leu Asn Arg Trp Leu Leu
145                 150                 155                 160

Ser Thr Phe Thr Gly Thr Phe Ala Ile Gly Leu Phe Phe Leu Thr Phe
                165                 170                 175

Leu Pro Tyr Phe Tyr Ile Ile Thr Tyr Leu Phe Ile Lys Thr Arg Ser
            180                 185                 190

Cys Ser Met Leu His Lys Ala Leu Thr Leu Val Pro Leu Thr Thr Trp
        195                 200                 205

Leu Ser Leu Phe Ser Met Leu Leu Phe Ser Ser Ser Ile Ser Ile Leu
    210                 215                 220

Ile Gln Gly Val Leu Trp Lys Arg Thr Gly Ser Leu Pro Ser Cys Thr
225                 230                 235                 240

Leu Trp Ser Leu Leu His Ser Leu Leu Leu Ser Thr Leu
                245                 250


<210> SEQ ID NO 15
<211> LENGTH: 312
<212> TYPE: PRT
<213> ORGANISM: Rattus norvegicus

<400> SEQUENCE: 15

Met Arg Leu Trp Asn His Thr Gly Val Glu Glu Phe Ile Leu Val Gly
1               5                   10                  15

Leu Thr Glu Asn Leu Asn Trp Gln Val Gly Leu Phe Phe Leu Phe Ser
            20                  25                  30

Ile Val Tyr Phe Ile Ile Leu Val Gly Asn Trp Gly Met Ile Leu Leu
        35                  40                  45

Ile Trp Leu Asn Ala His Leu His Thr Pro Met Tyr Phe Phe Leu Ser
    50                  55                  60

Asn Leu Ser Phe Cys Asp Ile Cys Tyr Ser Thr Val Ile Ala Pro Lys
65                  70                  75                  80

Met Leu Ile Asn Phe Leu Ser Glu Tyr Lys Ser Ser Thr Phe Phe Gly
                85                  90                  95

Cys Val Ile Gln Ser Phe Phe Phe Ala Val Tyr Ile Thr Thr Glu Val
            100                 105                 110

Ile Leu Leu Ser Met Met Ala Tyr Asp Arg Tyr Val Ala Ile Ala Asn
        115                 120                 125

Pro Leu Met Tyr Thr Val Ile Met Thr His Ser Ile Cys Ser Gln Met
    130                 135                 140

Val Leu Ala Cys Tyr Leu Gly Gly Leu Ile Asn Ser Leu Thr His Thr
145                 150                 155                 160

Ile Gly Leu Leu Arg Leu Asp Phe Cys Gly Pro Asn Ile Val Asp His
                165                 170                 175

Phe Phe Cys Asp Ile Pro Pro Leu Leu Lys Leu Ser Cys Ser Asp Ala
            180                 185                 190

His Ile Asn Glu Met Leu Leu Leu Leu Phe Ser Gly Val Ile Ala Ile
        195                 200                 205

Phe Thr Phe Ile Ile Val Met Val Ser Tyr Ile Gln Ile Ile Ile Ala
    210                 215                 220

Ile Leu Arg Ile Arg Ser Ala Glu Gly Arg Arg Lys Ala Phe Ser Thr
225                 230                 235                 240
```

```
Cys Ala Ser His Leu Thr Ala Val Thr Leu Leu Tyr Gly Ser Val Thr
                245                 250                 255

Phe Ser Tyr Ile Gln Pro Ser Ser Gln Tyr Ser Met Glu Gln Glu Lys
            260                 265                 270

Val Ser Ala Val Phe Tyr Thr Leu Val Ile Pro Met Leu Asn Pro Leu
        275                 280                 285

Ile Tyr Ser Leu Arg Asn Lys Asp Val Lys Glu Ala Ala Lys Arg Ser
    290                 295                 300

Ile Cys Arg Glu Ser Gly Gly Pro
305                 310


<210> SEQ ID NO 16
<211> LENGTH: 315
<212> TYPE: PRT
<213> ORGANISM: Mus musculus

<400> SEQUENCE: 16

Met Asn Thr Asn Asn Val Thr Tyr Leu Asn Pro Gly Thr Val Ile Leu
1               5                   10                  15

Ile Gly Ile Pro Gly Leu Glu His Val Gln Phe Trp Ile Gly Phe Pro
            20                  25                  30

Phe Phe Thr Val Cys Leu Val Ala Leu Leu Gly Asn Ile Ile Leu Leu
        35                  40                  45

Ile Ile Ile Pro Ala Glu Arg Ser Leu His Gln Pro Met Tyr Ile Phe
    50                  55                  60

Leu Ala Val Leu Ala Gly Thr Asp Ile Gly Leu Cys Ala Ala Ile Ala
65                  70                  75                  80

Pro Lys Met Leu Ala Ile Phe Trp Phe Arg Ala Tyr Ser Met Ala Phe
                85                  90                  95

Asp Ala Cys Leu Ala Gln Leu Phe Phe Ile His Thr Leu Gln Cys Met
            100                 105                 110

Glu Ser Gly Ile Leu Leu Ala Met Ala Phe Asp Arg Tyr Ile Ala Ile
        115                 120                 125

Cys Asp Pro Leu Arg His Thr Ser Ile Leu Thr Pro Ser Ile Leu Gly
    130                 135                 140

Arg Met Ile Val Val Val Val Ile Arg Ala Val Val Leu Val Gly Leu
145                 150                 155                 160

Leu Pro Ile Leu Ile Lys Arg Leu His His Phe Trp Ser Ile Gln Ile
                165                 170                 175

Ala His Ser Tyr Cys Glu His Met Ala Val Val Lys Leu Ala Ala Asp
            180                 185                 190

Asp Val Gln Val Asn Lys Ile Cys Gly Leu Phe Val Gly Phe Ser Ile
        195                 200                 205

Leu Gly Phe Asp Met Val Phe Ile Ile Ile Ser Tyr Ala Leu Ile Phe
    210                 215                 220

Gln Ala Val Phe Arg Leu Lys Gln Lys Glu Ala Arg Leu Lys Ala Phe
225                 230                 235                 240

Asn Thr Cys Thr Ala His Ile Phe Val Phe Leu Glu Phe Tyr Ile Leu
                245                 250                 255

Ala Phe Phe Ser Phe Phe Ser His Arg Phe Gly His Val Val Pro Ser
            260                 265                 270

Thr His Ile Leu Leu Ser Thr Ile Tyr Leu Leu Leu Pro Pro Ala Leu
        275                 280                 285

Asn Pro Ile Val Tyr Gly Val Lys Asn Met Val Ile Arg Lys Arg Val
    290                 295                 300
```

Ala Gln Ile Phe Phe Leu Asp His Ala His Gln
305 310 315

<210> SEQ ID NO 17
<211> LENGTH: 314
<212> TYPE: PRT
<213> ORGANISM: Mus musculus

<400> SEQUENCE: 17

Met Gly Pro Ala Asn Lys Ser Gln Leu Ser Pro Ser Thr Phe Trp Leu
1 5 10 15

Met Gly Ile Pro Gly Leu Glu His Leu His Val Trp Ile Gly Ile Pro
20 25 30

Phe Cys Ser Met Tyr Met Val Ala Leu Met Gly Asn Val Thr Ile Leu
35 40 45

Ala Val Val Arg Ala Glu Arg Thr Leu His Glu Pro Met Phe Leu Phe
50 55 60

Leu Cys Met Leu Ser Val Thr Asp Leu Val Leu Ser Thr Ser Thr Leu
65 70 75 80

Pro Arg Met Leu Cys Leu Phe Trp Met Glu Ala His Asp Ile Thr Phe
85 90 95

Asp Ala Cys Leu Ala Gln Met Phe Phe Ile His Ser Phe Thr Ala Met
100 105 110

Glu Ser Gly Phe Phe Leu Ala Met Ala Ile Asp Arg Tyr Val Ala Ile
115 120 125

Cys Asp Pro Leu Arg His Thr Thr Ile Leu Thr Asn Ser Arg Ile Ala
130 135 140

Lys Met Gly Ala Val Val Val Leu Arg Gly Val Gly Phe Phe Ser Pro
145 150 155 160

His Pro Ile Leu Leu Lys Gln Leu Pro Tyr Cys Arg Thr Arg Ile Ile
165 170 175

Ala His Thr Tyr Cys Glu Phe Met Ala Val Val Lys Leu Ala Cys Val
180 185 190

Asp Thr Gly Ala Thr Lys Arg Tyr Ser Leu Ser Val Ala Ser Val Ile
195 200 205

Gly Ser Cys Asp Gly Phe Phe Ile Ala Leu Ser Tyr Val Leu Ile Leu
210 215 220

Arg Ala Val Phe Arg Leu Pro Ser Arg Glu Ala Ser Leu Lys Ala Leu
225 230 235 240

Gly Thr Cys Gly Ser His Val Cys Val Ile Leu Val Phe Tyr Ser Thr
245 250 255

Ala Val Phe Thr Phe Leu Thr His Arg Phe Gly His Asn Val Ala Pro
260 265 270

Gln Ile His Ile Phe Ile Ala Asn Met Tyr Leu Leu Val Pro Pro Phe
275 280 285

Leu Asn Pro Ile Val Tyr Gly Ile Arg Thr Lys Lys Ile Arg Glu Tyr
290 295 300

Val Leu Ser Phe Leu Arg Val Lys Phe Ser
305 310

<210> SEQ ID NO 18
<211> LENGTH: 316
<212> TYPE: PRT
<213> ORGANISM: Mus musculus

<400> SEQUENCE: 18

-continued

```
Met Gln Asp Asn Thr Glu Phe Leu Ser Asn Phe Thr Ser Gln Leu Pro
1               5                   10                  15

Thr Phe Leu Leu Thr Gly Ile Pro Gly Leu Glu Ser Ala His Ser Trp
            20                  25                  30

Ile Ser Ile Pro Phe Cys Cys Leu Tyr Ala Thr Ala Leu Ser Gly Asn
        35                  40                  45

Ser Met Ile Leu Phe Ile Ile Val Thr Gln His Ser Leu His Glu Pro
    50                  55                  60

Met Tyr Tyr Phe Leu Ser Val Leu Ser Ala Thr Asp Leu Gly Leu Thr
65                  70                  75                  80

Phe Ser Thr Met Ser Thr Thr Leu Arg Ile Leu Trp Phe Gln Ala Asn
                85                  90                  95

Glu Ile Ser Leu Asp Phe Cys Ile Val Gln Met Phe Phe Leu His Gly
            100                 105                 110

Phe Thr Phe Ile Glu Ser Gly Val Leu Val Ala Met Ala Phe Asp Arg
        115                 120                 125

Tyr Val Ala Ile Cys Asn Pro Leu Arg Tyr Thr Met Ile Leu Thr Asn
    130                 135                 140

Ser Arg Ile Ile Gln Met Gly Phe Leu Val Ile Met Arg Ala Leu Leu
145                 150                 155                 160

Leu Ile Val Pro Leu Leu Leu Leu Leu Lys Pro Val Ser Phe Cys Lys
                165                 170                 175

Arg Asn Thr Leu Ser His Ser Tyr Cys Tyr His Pro Asp Val Ile Lys
            180                 185                 190

Leu Ala Cys Ser Asp Thr Arg Ala Asn Ser Ile Cys Gly Leu Val Asp
        195                 200                 205

Leu Ile Leu Thr Thr Gly Ile Asp Thr Pro Cys Ile Val Leu Ser Tyr
    210                 215                 220

Ile Leu Ile Ile Arg Ser Val Leu Ser Ile Ala Ser Ser Glu Glu Arg
225                 230                 235                 240

His Lys Thr Phe Ser Thr Cys Val Ser His Ile Gly Ala Val Ala Val
                245                 250                 255

Phe Tyr Ile Pro Met Phe Ser Leu Ser Leu Val His Arg Tyr Gly Arg
            260                 265                 270

Ser Ala Pro Lys Val Val His Thr Met Met Ala Asn Val Tyr Leu Leu
        275                 280                 285

Leu Pro Pro Val Leu Asn Pro Ile Ile Tyr Ser Val Lys Thr Lys Gln
    290                 295                 300

Ile Arg Lys Ala Ile Leu Ser Leu Leu Phe Ala Lys
305                 310                 315
```

<210> SEQ ID NO 19
<211> LENGTH: 945
<212> TYPE: DNA
<213> ORGANISM: Rattus norvegicus

<400> SEQUENCE: 19

```
atgggagaga ataacaatgt cacagaattt gttctcctgg gcctcactca ggatcctact      60

ggacaaaaag cattgtttgt catgtttttg ctcatgtaca ttgtgacaat tgtgggcaac     120

ctgctcattg tggggacagt gattgccagc cctccttga attccccaat gtacttcttc     180

cttgcttttc tgtcactcat ggatgctgtt tattccactg ccatcttgcc caagttgctt     240

aaagacttag tttgtgataa aaagaccatc tctttcacag cttgtctggt tcagcttttt     300
```

-continued

```
gtagagcact tatttggtgg tgctgaggtc ttccttctgg tggtgatggc ctatgatcgc    360

tatgtagcta tttgtaagcc actgcattat ttaaccacca tgaatcaaca ggtttgtatc    420

tcacttttgg tggtagcctg ggttggagga tttgcacatg ctctagttca agttctctct    480

gtatataaac ttcctttctg tggacctaat gtcattgacc actttggctg tgacatgtat    540

ccattattgg cacttgtgtg cactgacact tactttattg gcctcacagt agttgccaat    600

aatggagcca tgtgtatgat agtctttgtc cttcttctat tctcctatgg aattatctta    660

agctccctta agactcacag tcaggaagga aggcgcaagg ccttgtccac ctgcagctcc    720

cacattatgg tggttgtcct tttctttgtt ccctgcatat tcatgtatgt tagacctgtc    780

tccaacttcc ctattgataa atctatttct gtttttata cagctatcac tcccatgttg    840

aatcctttaa tatatacatt gagaaattca gagattaaaa attctatggg aaagctctgg    900

tataaaatga taagtatagg gagagtaaga atttttgcat gttga                    945
```

```
<210> SEQ ID NO 20
<211> LENGTH: 924
<212> TYPE: DNA
<213> ORGANISM: Rattus norvegicus

<400> SEQUENCE: 20

atggctccaa taaaccagtc agttgtgacc atgttcttcc tgcaaaactt tgttgatgat     60

ccctggatcc agaatgttct cttttgcttt ttctttgcct tgttcgtggc agccatagct    120

ggcaatggcc tgattatcac agtcattcac agcagtgcca acctccacac tcccatgtac    180

ttcttcctag tcaatctttc cctcatggat gtgatttgca ctgtgacagt gttgcccaaa    240

gtcctgcaga gcctggtggc agagaacgcc atttcttatg gggatgtct cacacagatg     300

tttgtcttct cctgggttct gggctctgag cttctgcttt tctctgccat ggcctacgac    360

cgctaccttg caatctgccg gccattgcac tatggtaccc tcatgagtgg cagggtctgc    420

atagcccttg caacctttgt gtggttcact ggagctctca attccttggt gctcacttgt    480

ctggtgttgc cactgtcctt ctgtggtccc aatctcatca cacacttctt ctgtgagatc    540

ccttctgtgt tgatgctgtc ctgcagcccc acctttatca atgacatcat gactgtcatt    600

gcagacatgt tccttacagg cctgaacttc ctattgacta tgacatccta tggctttatc    660

attgccagca tcctgcgcat ccgctctgct gagggcaaga agcgtgcctt ctctacctgc    720

tctgcccacc tggttgtggt caccctttat tattctactg ttctatatac ttatgtccgg    780

ccagccctag gaacttctgg gctcctggac aaagtcattg ctgttctgta taccactgtg    840

accccatctc tgaacccact catctatacc ctgagaaaca aggaattcaa aacatccttt    900

aaaaaactct tatttcccaa ttga                                            924
```

```
<210> SEQ ID NO 21
<211> LENGTH: 930
<212> TYPE: DNA
<213> ORGANISM: Rattus norvegicus

<400> SEQUENCE: 21

atggaaacaa taaataaaac tgccaagata aatttcttct ttcgcccatt ctcatctgac     60

cctggggtgc agatggtgat ttttgtgacc ttcttagtga tgtacctgac cagcctcagc    120

ggtaatgcta caattgctgt gattgtccac attaaccatg cactgcacac tcccatgtac    180

ttttttctag ctaacttggc agttctggaa atcttctata catcatccat tgcaccactg    240

gccttggcaa accttctttc tatgggtaaa acccctgttt ccatcactgg ttgtggtacc    300
```

-continued

```
cagatgtttt tctttgtttt cttgggtggg gctgactgtg tcctgcttgc agtcatggct    360
tacgaccggt ttgttgcaat ctgctaccct ctgagataca cactcatcat gagctggtcc    420
ttgtgtgtag agatgatggt ggggtccctg gtgctgggat gcctgctgtc actgccccta    480
actattttaa tcttccatct gccattctgt cacaacaatg agatctacca cttctactgt    540
gacatgcctg cagtcatacg cctggcttgt ggagacacgc acgttcatag gacagccctg    600
tacatcatca gcttcattgt cctaagcatc cccctaactc tgatttctat ctcctatgtc    660
ttcatcatca cggccatttt acggatccgg tctgctgaag ggcgccatcg agccttctct    720
acctgctcct ctcacattgt agtggtcctc ctacaatatg gctgcaccag ttttatatat    780
ttatccccca gttccagcta ctctcctgag atgggcagaa tggtgtctgt ggtctacact    840
ttcatcaccc ccatcttaaa ccctttgatc tatagtatga ggaacaagga actaaaagat    900
gctctgagga aggcattgaa aaagttctag                                    930
```

<210> SEQ ID NO 22
<211> LENGTH: 933
<212> TYPE: DNA
<213> ORGANISM: Mus musculus

<400> SEQUENCE: 22

```
atgatgaatt ctaccatggt gactgagttc ctcctggagg tttttgctga gacttgggag     60
ctcagggtcc tactcagtgt gctgttcctg ctggtgtacc tgggcagcct gttcgggaat    120
cttaccatca tcattgttac tacagttgac cagaccctga acacacccat gtacttcttc    180
ctcaggaatc tgtccatctt agacatgtgc tatgtttcta ttactgtgcc caatgcctgt    240
ataaactctc tcactgacca caggaacatt tctgtgactg ggtgtgcagc acagatcttt    300
ttgttcttct tttgtgcatg tgtagaggtt cagtttctca ccatcatggc tcaggaccgc    360
tatgtggcca tatgcaagcc tctcctctac cctatgatta tgaaccatca attctgtgtt    420
cagatgacac tggcttccct acttacctca cttatccttt caggtatgaa cactttcaaa    480
actttccagc tgtccttttg tcactcaaat gtagttcctc agttcttctg tgagctgcct    540
gctttgctga ggcttacttg ctctgacacc tttaacaaca aaatcatact tcttctgact    600
gccattggcc ttagtggtac ctgctttact ttcattgcca tatcatatgt tcacatatta    660
tcaactgtct tgaaagttcc tgtcaaagga gagagaggga aagccttttc tacctgtgtc    720
cctcacatca ttgtagcata tttgtttctt tgttctggtg cctatgcata tctaagacct    780
ccagcaatct cagaagtagt tgaggatatg actctttctg tattttatac cactgttcct    840
ccattcttaa accctattat ctatagcctt agaaacaaac aaataaagaa ggctgtgaag    900
aaagtaatat tcagattttt catagttgaa taa                                 933
```

<210> SEQ ID NO 23
<211> LENGTH: 780
<212> TYPE: DNA
<213> ORGANISM: Mus musculus

<400> SEQUENCE: 23

```
atggaagtta gaaatgtcac tgagtttgtg ctcctcggac taaccagcaa ccctcggagc     60
caggtggttc tctttgtgct gttcttggtg atttacctcc tgaccctcgt ggggaacctg    120
ctgatgctga tgctgatcag ctctgacgcc caccttcgta cccccatgta cttcttcctg    180
agatacctct ccttcatgga tgctttctac tcttcggtca ttgtgcccaa gttgctgagg    240
```

-continued

```
aaccttattt ctgagtggaa gaccatatcc ttccttgggt gtttcattca gatcgccctg    300

gtcatatttt ctggggccac cgaagcctgc ctcctttccg ccatggccta tgaccggttc    360

caggctgtgt gccacccgct gttgtatgtg gtcactatga atggaaaggt atgttctggg    420

atggtggcta tatcctgggc cgtaggaatg agcgttagcc tggttaacac cctcctgcta    480

gctcaggaga acttctgtgg cccgaacgtc atccacaatt ttgcttgtga gcttcctccg    540

gtgctcttgt tggtctgttc caacccccac actactattg cctccatcct gaccacgttg    600

gtgatcttgg gttttggttc acttatcctc ctgctgggat cctacagccg catcatcaag    660

acagccctgg gcgtcaactc ggccacaggt cggagcaaga tcttctccac atgttcctcc    720

catttccttg tggttaccat cttttatggt tcaggagtgt tcaggtgtgt cacgcggtag    780
```

<210> SEQ ID NO 24
<211> LENGTH: 945
<212> TYPE: DNA
<213> ORGANISM: Rattus norvegicus

<400> SEQUENCE: 24

```
atggaagaga ctaacaatgt tactgagttt atcctcctgg gtctcactca ggatcctgct     60

gggcaaaaag tattatttgt catgttttta ctaatctaca ttgtgacaat agggggcaac    120

ctgctcattg tggggacagt gattgccagc cctccttgg gctccccaat gtacttcttc     180

cttgcctttc tctcactcat ggatgctgtt tattctactg ccatcttgcc caagttgctt    240

acagatttac tttgtgataa gaaagccatc tctgtcaaag cttgtctagt tcagcttttt    300

gtggagcact tatttggtgg ttctgaggtc ttcattttgg tggtgatggc ctatgatcgc    360

tatgtggcca tctgtaagcc actgcactat ttgaccataa tgaatcggca agtttgcatt    420

ctcttgttgg tggtgtcctg ggctggagga tttgcacatg ctctgcttca agtgatctct    480

gtgtatttac ttcctttctg tggacccaat gtcattgacc attttgcttg tgacatgtac    540

ccattgttag gacttgcatg tactgatacc tacttccttg gactcagtgt aattggaaat    600

aatggagcaa tgtctatagt ggtctttatc ctcctccttg tctcctatgg aatcattcta    660

aactctctta agacctacag tcaggaaggg agacgcaaag ccctgtctac ctgcagctcc    720

cacatcatgg tggtcatcct cttttttgtt ccttgtattt tcatgtatgt tagacctgtg    780

tctaactttc caattgataa atatattact gtcttttata caatttttac tccaatgttg    840

aaccctttga tatatacctt aagaaatatg gagattaaaa attgtatggc aaagctgtgg    900

ggtaaaatgt tcactaaaga cataaaaaaa atttctgctc actga                     945
```

<210> SEQ ID NO 25
<211> LENGTH: 954
<212> TYPE: DNA
<213> ORGANISM: Rattus norvegicus

<400> SEQUENCE: 25

```
atggctatag gaaaccagac aagagtaact gagtttatcc tcatgagctt ctcttccctg     60

cctactgaaa tacagacctt gctcttcctg gcatttctca gcatctattt agtcactctg    120

ctgggaaaca gtctcattat tttggtgact ttggctgacc ccatgctgca aagccccatg    180

tatttccttc tcaggaactt agccttctta gagattggct ttaacctggt cattgtaccc    240

aaaatgttgg ggactctgat tgcccaagac acaagtatct ccttcctagg ctgtgccact    300

cagatgtatt tcttcttctt ctttggagta gctgagtgct tcctcctggc caccatggcc    360

tatgaccgct atgtagccat ctgcagtccc ttacattacc cagtcattat gaaccaaggg    420
```

```
acacgtgcca gactggctgc tgcttcctgg tttccaggat tccctgtagc cactgtgcag    480

accacatggc tcttcagttt tccattctgt gccaacaaca aggtgaacca cttcttctgt    540

gacagcccac ctgttctgag gcttgtctgt gcagacacag cacggtttga ggtctatgcc    600

attgttggaa ccattttggt ggtcatgata ccctgcctgc tgatcctttg ttcctacact    660

ctcattgtag cttccatcct caagattcca tcagcacaag ggaagcacaa agccttctcc    720

acctgctcct cacatctgct tgttgtctct cttttctatg tgtcttcaag cctcacttac    780

tttaggccta aatcaaataa ttctcctgaa agcaaaaagt tgttatcatt gtcctacact    840

gttgtgactc ccatgttgaa ccccattatc tatagcctga gaaataatga ggtgaagaat    900

gccctcagca ggaccttcta caaggcgctg gccctcagaa atcatattac ttaa          954
```

<210> SEQ ID NO 26
<211> LENGTH: 951
<212> TYPE: DNA
<213> ORGANISM: Rattus norvegicus

<400> SEQUENCE: 26

```
atgaacctag gtaatgaaag tgctccaaag atcttcattc ttttgggttt ctccaactat     60

ccatggctgg aaatgcccct cttcataatg gtgcttgttg cttatgtctg cacagtggtg    120

ggaaatatat caattattgt tgtatccaag atagaccctc aactggacag cccaatgtac    180

ttcttccttt ccaacctctc cttcttggac ctgtgtttca ccacaaccac catccctcag    240

ctacttcgga atctttgggg cccagataaa tccatcagct acagaggttg tgtaacacag    300

ttttatattt ttcatttcct tggggctact gagtgcatcc tcctggctgt gatgtctttg    360

gatcgttaca ttgccatatg caagcccctg aggtacccag caatcatgca ccagcaattc    420

tgtatcctcc tcatgttcat gacatggctg agtggtttgg ctaattcttt gcttcaatca    480

accctcactg tcaagctgcc attttgtgga aacaacaagg tagacaactt tctctgcgag    540

gtcccagtga tgatcaagat gtcctgtgct aacactgcat tcaatatagc tatgctctcc    600

attgtaggga ctttctactc tctggttccc ttgtcactta ttcttgtttc ctatgggttc    660

attgtagcga cggtacttag gattcgttcc tcagagggca agaagaaagc ctttaataca    720

tgtggctctc atgttgttgt tgtgactctt ttctatggac cagtaattag catgtatgta    780

caaccttcat cttctagttc tcaggacaag aacaaacttc tgtctctgtt ttacagtttg    840

gtgactccta tgcttaaccc ttttatttat actttgagga acaaggatgt gaagggagca    900

atgaggagat ttcttgtctc attgtttcac aaggaatcgg agcaaacata a             951
```

<210> SEQ ID NO 27
<211> LENGTH: 939
<212> TYPE: DNA
<213> ORGANISM: Rattus norvegicus

<400> SEQUENCE: 27

```
atgaatggag gaaatcagtc tgagctgtca gaatttgtgc ttttgggact tttcgctca     60

cagaatcttc aggttgtgct ctttgtgata tttttgatat tttacctgct cattgtttca    120

ggaaacattg tcatcatgtt cttaataacc attgaccgtc atctccattc ccctatgtac    180

ttcttgttgg ccaatctgtc ctttgttgat atatggcttt cctcagttac cactccaaaa    240

atgatcacag actttctcag ggaacacaag accatttcct ttgcaggatg catgtcccag    300

gtcttctttg cccattgcat tgctgcagga gagatggtgc tcttgctggt gatggcttat    360
```

```
gaccgctatg tggccatctg caaaccactc cactatttca ccatcatgaa cttgagaaga    420

tgcactggat tggtgttgac atcctggact gttggctttg tgcatgcctt gagtcagctt    480

gtagcagttc tgcagctacc tctctgtggc ccattggaaa tagacagttt tttctgtgac    540

atgccactgg taatcaagct cgcctgcata gattcccatg atttggacat gttaatgaat    600

gctgactgtg ggatagtggt tgtatcctgc tttattctgt tactcatatc ctacacatat    660

atccttgtca ctgttcacag gagcgctaaa gctggagcat ctaaggccct gtccacatgc    720

actgcccaca tcaccgtggt gatgctcctt tttctgccct gcatcttcat ctatgtgtgg    780

cccctcaata tcacctggtt ggacaaattt cttgctgtgt tttattctgt tgttacacct    840

ctcctaaatc cagccattta tacactgaga aacaaagaaa taaaaaatgc tctaaagaga    900

tttaaaagct atgttattaa tcacaaggta aatacttaa                           939


<210> SEQ ID NO 28
<211> LENGTH: 939
<212> TYPE: DNA
<213> ORGANISM: Rattus norvegicus

<400> SEQUENCE: 28

atgattaaag gaaaaaacat tactgagatc acccagttca tcctcctggg attctctgat     60

ttcccccaaa tcacagcact gctctttgtt atattcctca ccctgtacat tacagcactg    120

acctggaacc tgtcccttat tgttttaata aggatggact cctacctcca cacacctatg    180

tacttcttcc tcagcaatct ggcctttatt gacctctgct atatcacttc tacagtccca    240

aagatgcttt ccaacttctt ccaggaaaag caaactatca gttttgtgga ctgtattgtt    300

caatacttta tcttgtccac tatggggctg actgaatcct gcctcatgac agtcatggcc    360

tatgacaggt atgctgccat ttgtaaccct cttctctact catcaatcat gtcacccagt    420

ctctgtgctc ggatgctctt gggaagctat gcagcaggac ttgtgggttc tgtatctcag    480

gtgtgtgcct tgctgcagct ccatttctgt ggatctaatg tcatcagaca tttcttctgt    540

gacatgcccc agctgttaaa tctatcctgc attgatactc tttttgcaca gatccttctt    600

gctgtattaa caacattatt tggtttttca aatgccttag ccatcatgat atcctatggc    660

catattatct tgtccatcat gaagatcacc tcagttaagg gcaggtccaa gtccttcaac    720

acttgtgctt ctcatgtgac agcagtttcc ctgttctaca cctctagtgt ctttgtctat    780

ttgagttcca gctctggtgg ctcctccagc tttgacagat ttgcatctgt cttctacaat    840

gtgatgattc caatgttgaa ccctttggtt tacagtctga ggaacaagga aattagagat    900

gctgtaaaga ggctaaagaa gaagctggga tgctgctaa                           939


<210> SEQ ID NO 29
<211> LENGTH: 936
<212> TYPE: DNA
<213> ORGANISM: Rattus norvegicus

<400> SEQUENCE: 29

atgcagaatc agagttttgt caatgagttc atactcttgg ggctttctca gaacccaaaa     60

gttgagaaaa tactatttgt tgtatttttta ttggtctata ttgcaactat tgggggcaat    120

ataatgattg tggtgaccat catctacagc cctgcactgc tgggctcccc catgtatttc    180

ttcttgatat tcttgtcctt actggatgca tgtacttctt ctactgtcac ccccaagatg    240

attgtagact tcttctatga gaggaagacc atctcctttg aatgttgcat cacacaattg    300

tttaccagcc acttctttgc aggagttgag gtgattatct tgacatctat ggcttatgac    360
```

cgctatgtgg ctatctgcaa gcctcttcac tattcttcaa tcatgacccg gaggctctgt 420
ggcactcttg taggggtggc ctggacagga ggattcttac attctatcac acaagttatc 480
tttacgttgc agctaccatt ctgtggaccc aattttattg atcatttcat atgtgacttg 540
ttcccattac tgcagcttgc ctgcactgac acacacattt ttgtcatttt ggtgtttgct 600
aacagtggct ctttctgcat cattatcttc tctttgttga ttatctccta tggcgtcatc 660
ctcttctctc taagaggtca cagctcagaa ggacgaagga aagctctctc aacctgtgga 720
tcccacatta ctgttatgat tttgttcttt gtcccatgca tgctaatata tgcacggcct 780
tcatctgcct tttcctttga gaaaaacaca cttatatttg cctctgtcct gacaccattg 840
ctcaatccta tggtttacac tttcagaaat aaagaaatga agaatgccat caggaaaatg 900
agtaggaaat taatagtggt ttctaataca ttttaa 936

<210> SEQ ID NO 30
<211> LENGTH: 967
<212> TYPE: DNA
<213> ORGANISM: Rattus norvegicus

<400> SEQUENCE: 30
atgggaggtg tcaaccaaac aactatatca gaattcattc ttctggggct tagtgatgat 60
ccagctctgc agcctttcat ctttaccctg ttcctgtcca tatatctgat caccacctta 120
ggaaacctgc tcatcattct agctgttagc tttgactccc aactacacac gcccatgtat 180
ttctttctct ccaacctgtc ttttaatgac atctgtataa tcacaaccac aatcccaaag 240
atgctgatga acgtccaatc ccatgatcaa tccatcacat ataaaggatg cctctctcag 300
gtctacctca ttgtgaattt tggtagcata gaaagttgtt tacttgcagt gatggcctat 360
gaccgctatg ttgctatctg ccaccctctg aagtacacag ttatcatgaa tcactatttt 420
tgtgtgatgc tgctgctctt ctctgtgttc gttagcattg cacatgcgtt gttccacatt 480
ttaatggtgt tgatactgac tttctgcaca aaaactgaaa tccctcactt tttctgtgag 540
ctggctcata tcatcaaact tacctgttcc gataatttta tcaactatct gctgatatac 600
acagtgtctg tcttattttt tggtgttcat attgtaggga tcattttgtc ttatatttac 660
actgtatcct cagttttaag aatgtcatta ttgggaggaa tgtataaagc cttttcaaca 720
tgtggatctc atttgtcggt tgtctctgtt ttatggcaca ggttttgggg tacacataag 780
ctctccactt actgactctc caaggaagac tgtagtggct tcagtgatgt acactgtggt 840
tactcagatg ctgaacccct tcatctacag cctaaggaac aaagacataa agccttcaga 900
aaaatcatta ataggatact acatatttta taataaatca tcatttatat caaagttttt 960
agagtaa 967

<210> SEQ ID NO 31
<211> LENGTH: 815
<212> TYPE: DNA
<213> ORGANISM: Rattus norvegicus

<400> SEQUENCE: 31
atgtttggga atggagccat catgatgatc gtcagcttag atccaagact ccactcacct 60
atgtacttct tcctgggaaa cctagcatgt ctagatatct ccttctccac tgtaacagtg 120
ccaaagatgc ttgagaactt ctccataagc aaagcaattt ccttcttggg atgcataact 180
cagctttatt tcttccactt cctgggtagc acagaggcct tactgctgac aatcatggcg 240

-continued

```
tttgaccact ttgtggctat ctgcagacca ctccactacc cttccatcat gaatcatcag    300

gtgtgtatcc agagggctgt cttcatctgg gccactcctt ttctccatgc tctggttcac    360

tccagattga cgtctcgatt aaacttttgt agttccaaca atgtccatca tttcttctgt    420

gatgttaagc cattattgga actggcctgt ggaaacactg aactcaacag gtggctgctc    480

agtacattca cagggacatt tgccattggc cttttctttc tgacatttct cccctatttc    540

tacatcatca cctatctctt tatcaaaacc cgttcttgta gcatgttgca caaagcattg    600

acacttgtgc ctctcactac atggttgtca ttattttcta tgctcctgtt ctcttcatct    660

atatcaatcc tgattcaggg agttctctgg aaaaggacag gatcattgcc gtcatgtaca    720

ctgtggtcac tcctgcactc actcctgtta tctacactat gaggaacaag gaagggaggg    780

gtgctctgaa taggaaaatc agaatacagc tttga                               815
```

<210> SEQ ID NO 32
<211> LENGTH: 939
<212> TYPE: DNA
<213> ORGANISM: Rattus norvegicus

<400> SEQUENCE: 32

```
atgagactct ggaatcatac aggtgtggag gaattcatac tagtcggatt aacagaaaac     60

cttaattggc aagtcgggct ctttttcctt ttcagcatag tttattttat cattcttgtg    120

ggtaactggg ggatgattct tttgatctgg ttgaatgccc atcttcatac tccaatgtac    180

ttctttctta gtaacctctc tttttgtgac atctgctatt ctactgtcat tgctcctaaa    240

atgctcatta atttcctgtc agaatacaag tctagcacat tctttggttg tgttattcag    300

agtttctttt ttgcagtgta tataactaca gaagttatac tcttgtctat gatggcttat    360

gatcgttatg tggcaattgc aaacccctta atgtatacag ttattatgac acacagcatc    420

tgcagtcaga tggttcttgc atgttacttg ggtggcctta ttaattccct gactcacaca    480

ataggtttac tcagactgga cttctgtggt cccaacattg tagaccattt cttctgtgac    540

atccctcctc ttttgaagct ttcatgttct gatgcacaca tcaatgagat gctgcttttg    600

ttattctctg gagtgattgc tatttttact ttcatcattg tcatggtgtc ctatattcaa    660

attatcattg ccatcctgag aatccgctca gctgagggaa ggcgtaaagc cttctcaact    720

tgtgcctcac atctaacagc tgtgacatta ctttatggtt ctgtgacatt tagctatatc    780

caaccaagtt ctcaatattc catggaacag gaaaaagtct ctgcggtgtt ttacaccttg    840

gttatcccca tgttgaaccc tctaatttac agcctgagga acaaagatgt gaaagaggca    900

gccaagaggt caatttgtag ggagagtggt ggcccttga                           939
```

<210> SEQ ID NO 33
<211> LENGTH: 948
<212> TYPE: DNA
<213> ORGANISM: Mus musculus

<400> SEQUENCE: 33

```
atgaacacca ataacgtgac atatctgaac cctggaactg taatactgat tggaattcct     60

ggactagagc acgtgcagtt ttggattgga tttccattct ttacagtgtg tctggtggct    120

cttttgggaa atatcatttt attaatcatc atcccagccg agcgtagctt acaccaaccc    180

atgtacatct tcctggctgt gctggcaggt acagacatag gactttgtgc agccattgcc    240

cccaaaatgt tggccatatt ttggttcagg gcttattcca tggcctttga tgcctgccta    300

gcccaactct tcttcatcca taccttacag tgcatggagt ccggcattct attggcaatg    360
```

-continued

```
gcttttgatc gatacattgc aatctgtgat cctctgaggc acacatctat tcttacacct    420

tcaattcttg gtcggatgat agtggtggtg gtaattcgag cggtagtact tgtaggcctg    480

ttacctattc taataaaaag actgcaccat ttttggtcca ttcaaattgc ccactcttac    540

tgtgaacaca tggctgtggt gaagcttgca gcagatgatg tacaggtcaa taagatatgt    600

ggtctttttg tggggtttag cattctggga tttgacatgg tttttatcat catatcatat    660

gccctgattt tccaagctgt ttttcgcctt aaacagaagg aggcaaggct caaagccttt    720

aacacctgca cagctcatat ttttgttttt ttagagttct atattcttgc ctttttctcc    780

ttttttagcc accgttttgg tcatgttgtt ccctccactc acattcttct gtcaaccatc    840

tacctcctct tgcctcctgc tctcaaccct attgtgtatg gagtaaaaaa catggtcatt    900

cgaaagcggg ttgcacagat ctttttttcta gatcatgcac atcagtag                948
```

```
<210> SEQ ID NO 34
<211> LENGTH: 945
<212> TYPE: DNA
<213> ORGANISM: Mus musculus

<400> SEQUENCE: 34

atggggccag ctaataagtc acaactctct ccaagcacct tctggctgat gggcatccca     60

ggcctagaac acctccatgt ctggattggg attcctttct gttccatgta catggtggcc    120

ctgatgggga atgtgactat cctggccgtg gtgagagcag agcgcaccct ccacgagccc    180

atgttcctct tcctgtgcat gctgtctgtc actgacctgg tcctctccac atctacattg    240

ccacgcatgc tctgtctctt ctggatggaa gcccatgata tcaccttcga tgcatgcctt    300

gctcaaatgt tcttcatcca tagtttcact gccatggaat ctggcttctt cttggccatg    360

gctattgatc gctatgtggc catttgtgac ccactacgtc ataccactat tctcaccaac    420

agtcgcatcg ccaagatggg ggcagttgtg gtgctgcgtg gggtaggctt tttctcccca    480

caccccatcc tgctcaagca gctgccctac tgcagaactc gaatcattgc acacacctac    540

tgtgagttca tggctgtggt gaagctggca tgtgtggaca caggagctac caagcgttat    600

agcctcagtg tggcctctgt cattggttct tgtgatggct tcttcattgc cctctcttac    660

gttcttatcc tccgtgctgt ttttcgtctt ccatctcgag aagcaagtct taaagcctta    720

ggaacctgtg gctcccatgt ctgtgtaatc cttgttttct attctacagc cgtctttaca    780

ttcctgaccc accgttttgg ccacaatgtg gccccccaaa ttcatatctt catagccaat    840

atgtaccttc tggtaccgcc ctttctaaac ccccattgttt atggtattag aacaaagaaa    900

attagagagt acgttcttag ttttcttaga gtaaaatttt cctga                    945
```

```
<210> SEQ ID NO 35
<211> LENGTH: 951
<212> TYPE: DNA
<213> ORGANISM: Mus musculus

<400> SEQUENCE: 35

atgcaggaca acacagaatt cctaagcaac ttcacatcgc aattaccaac cttcttgttg     60

actggcattc ctggcctaga gtctgctcac agctggatct ccatcccttt ctgttgtctt    120

tatgccactg ccctctctgg caacagcatg atcctcttca tcattgtgac ccagcatagt    180

ctgcatgaac ctatgtacta tttcctctct gtgctctctg ccactgacct aggtttgact    240

ttttctacaa tgtcaactac cttgagaatc ctgtggtttc aggcaaatga aatcagtcta    300
```

-continued

```
gatttttgca ttgttcagat gtttttctc catggattca catttataga atctggagtg    360
ctagtggcta tggcttttga tcgttatgta gcgatctgca accctcttag atataccatg    420
attcttacta attctagaat cattcagatg ggtttcctag tgataatgcg tgctctgtta    480
ttaatagtcc cactgcttct gctccttaaa cctgtctctt tctgtaaaag gaataccctc    540
tcccactcct actgttatca tccagatgtg attaagttag catgttcaga cactcgagcc    600
aatagcatct gtggactagt tgatctcatt ctgaccacag ggatagatac tccatgcatt    660
gtcttatctt atatactgat cattcgctct gtcctcagta tcgcctcctc tgaagaaagg    720
cacaagacct tcagcacctg tgtgtcccac attggagcag ttgcagtttt ctacatccca    780
atgtttagcc tgtctctggt acatcgatat ggtcggtcag cacccaaggt agtccataca    840
atgatggcca atgtttacct tcttctaccc cctgtgctca accccatcat ctacagtgtg    900
aaaacaaaac aaatcagaaa ggctattctt agtttgctct ttgcaaaatg a             951
```

BIOSENSOR EXHIBITING SENSITIVITY TO TRINITROTOLUENE

CROSS-REFERENCE TO RELATED APPLICATIONS

This application claims priority to and is a non-provisional of U.S. Patent Application 62/440,773 (filed Dec. 30, 2016), the entirety of which is incorporated herein by reference.

STATEMENT OF FEDERALLY SPONSORED RESEARCH OR DEVELOPMENT

This invention was made with Government support under grant number W911NF-14-1-0376 (65344_LS)-ADD-ON awarded by the Defense Advanced Research Projects Agency (DARPA). The government has certain rights in the invention.

REFERENCE TO A SEQUENCE LISTING

This application refers to a "Sequence Listing" listed below, which is provided herewith as an electronic document which is incorporated herein by reference in its entirety.

BACKGROUND OF THE INVENTION

In mammals, olfactory perception of chemicals in an odor stream is based on the combinatorial activation of specific detectors, called odorant receptors (ORs). These proteins are expressed by olfactory sensory neurons (OSNs) that line the nasal cavity of mammals. The olfactory sheet is a broad chemical detector, in which each odorant receptor is equally distributed in the main olfactory epithelium (MOE) and only expressed in 0.1% of all OSNs in rodents. Each OSN expresses only one OR gene in a highly regulated way. Due to the combinatorial activation nature of odorant perception in mammals, each population of OSNs can be activated by various agonists and each agonist can be recognized by various odorant receptors. Expressing functional odorant receptors in vitro using mammalian cell lines has been problematic. Therefore, odor coding has been studied in vivo in the odorant receptor's native environment, i.e., in OSNs in a living animal such as a mouse or a rat.

Trinitrotoluene (TNT), or more specifically 2,4,6-trinitrotoluene, is a chemical compound with the formula $C_6H_2(NO_2)_3CH_3$ and is best known as an explosive material with convenient handling properties commonly used for military, industrial and mining applications. Due to the dangers associated with the legal and illegal uses of explosives, there is an urgent need for sensitive sensors allowing the detection of TNT in a variety of settings (war zones, weapon test grounds, mines, public areas at risk for attacks by terrorists etc.) and by various organizations (e.g. military, law enforcement etc.). In addition to its explosive properties, TNT is toxic to a variety of organism ranging from bacteria to humans. Skin contact with TNT can cause skin irritation, and long-term exposure to TNT may lead to anemia and abnormal liver functions. Since the rising use of TNT has resulted in contamination of soil and water in construction sites and weapon test grounds, the ability to easily and quickly detect TNT is also critical from a public health and environmental perspective.

Dinitrotoluenes (DNT) are highly toxic with a threshold limit value of 1.5 mg per cubic meter, converting hemoglobin into methemoglobin, i.e. a form of hemoglobin that is not able to bind oxygen. Dinitrotolenes are released in the environment primarily from facilities that manufacture or process DNT. Most DNT is used in the production of toluene diisocyanate, which is used to produce flexible polyurethane foams. It is not used by itself as an explosive, but some of the production is converted to TNT. Human exposure to 2,4-DNT and 2,6-DNT occurs through inhalation, dermal contact and incidental ingestion, usually in occupational settings. Human toxicity has been evaluated by the US Environmental Protection Agency in DNT factory workers, munition handlers, and underground mining workers. DNT-related effects have been noted in the central nervous system, heart and circulatory system. Other effects that are possibly due to 2,4-DNT and 2,6-DNT exposure include increased mortality from ischemic heart disease, hepatobiliary cancer, and urothelial and renal cell cancers. Biosensor that detect TNT (or DNT) can as such provide a means for early detection and prevention of DNT exposure contamination.

The discussion above is merely provided for general background information and is not intended to be used as an aid in determining the scope of the claimed subject matter.

BRIEF DESCRIPTION OF THE INVENTION

Biosensors for detecting trinitrotoluene (TNT) are disclosed. Contemplated biosensors comprise one or more populations of cells that preferentially express an odorant receptor protein given by any one of SEQ ID NO: 2-15.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3A is a Fragments Per Kilobase of transcript per Million reads mapped (FPKM) graph of both TNT-exposed and control responses for the candidate receptors while

DETAILED DESCRIPTION OF THE INVENTION

Figure 1:
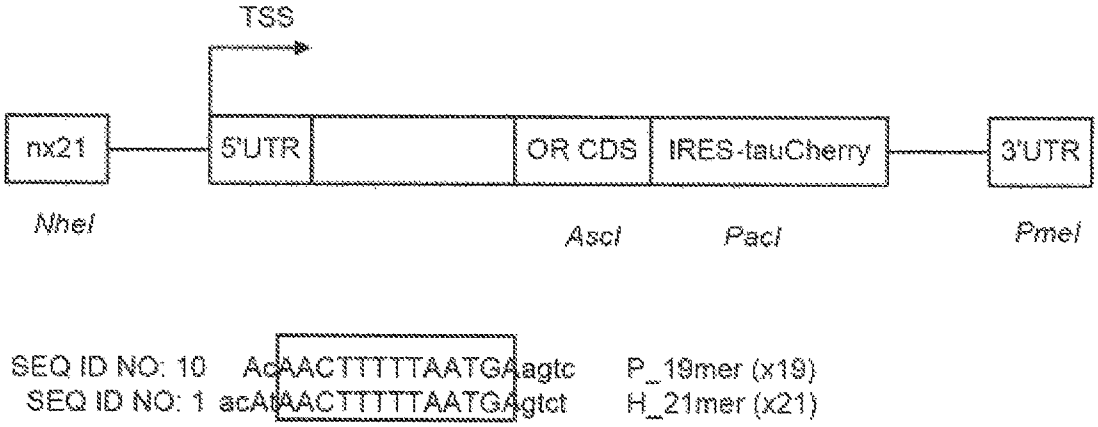
FIG. 1 depicts a schematic expression construct for the preferential expression of an odorant receptor (OR) containing a 5' and 3' untranslated region (UTR) flanking the coding sequence (CDS) of the OR and a co-expressed marker (in this case tauCherry)

Through the identification of odorant receptors (ORs) that bind to TNT, one can now preferentially express those specific TNT-responsive ORs in a population of olfactory sensory neurons (OSNs), for example, in the population of OSNs in the nose of a mammal, and as such decrease the detection threshold for TNT in this mammal. In addition, TNT-receptive ORs can now be functionally generated in vim (D'Hulst; C., Mina, R. B., Gershon, Z., Jamet, S., Cerullo, A., Tomoiaga, D., Bai, L., Belluscio, L., Rogers, M. E., Sirotin, Y., et al. (2016). MouSensor: A Versatile Genetic Platform to Create Super Sniffer Mice for Studying Human Odor Coding. Cell Rep 16, 1115-1125) or in vitro (Saito, H., Kubota, M., Roberts, R. W., Chi, Q., and Matsunami, H. (2004). RTP family members induce functional expression of mammalian odorant receptors. Cell 119, 679-691).

This disclosure describes methods and biosensors for the detection of TNT. In one embodiment, a biosensor comprises one or more populations of eukaryotic cells, wherein each cell population preferentially expresses a TNT-responsive OR. In one embodiment, the biosensor comprises a population of olfactory sensory neurons, or cilia derived thereof, wherein each population of olfactory sensory neurons, or cilia derived thereof, preferentially expresses a TNT-responsive OR.

In some embodiments, the biosensor is a genetically modified mammal. In some embodiments, the biosensor is a genetically modified rat, mouse, or a dog. In another embodiment, the biosensor is a chip or is utilized as part of a biochemical assay. The disclosed biosensor may be used to test a sample to detect the presence of TNT. In some embodiments, the concentration of TNT can be measured and/or quantified. The sample may be obtained from a subject, such as a human subject, or an environmental sample. When the biosensor is a chip or otherwise involves attachment of populations of cells or cilia to a solid support, the biosensor may comprise an array of individual populations each preferentially express a different TNT-responsive OR.

A TNT-responsive OR is an OR that binds to, and is activated in response to, exposure to TNT. A TNT-responsive OR includes rat ORs Olr710; Olr300; Olr319; Olfr297; Olr1109-ps; Olr711; Olr1664; Olr770; Olr387; Olr679; Olr1157-ps; Olr1725-ps and Olr550, as well as mouse ORs Olr227; Olr597, Olr605; and Olfr566.

The disclosed TNT biosensor can comprise one or more cell populations, wherein each cell population expresses one of the TNT-responsive OR genes represented by SEQ ID NO: 2-15. In one embodiment, the disclosed biosensor comprises one or more cell populations, wherein each cell population expresses an OR that has at least 85% similarity to one of the TNT-responsive ORs represented by SEQ ID NO: 2-15. In another embodiment, the disclosed biosensor comprises one or more cell populations, wherein each cell population expresses an OR that has at least 85% homology to one of the TNT-responsive ORs represented by SEQ ID NO 2-15.

In some embodiments, the biosensor comprises one or more cell populations, wherein each population preferentially expresses an OR that is a homolog or an orthologue of one of the TNT-responsive ORs represented by SEQ ID NO: 2-15. As used in this specification, a homolog of a TNT-responsive OR is an OR that shares 85% or more homology (amino acid identity plus amino acid similarity) as compared to a TNT-responsive OR. As used in this specification, an orthologue of a TNT-responsive OR is an OR (1) that is encoded by a gene that is located at an orthologous position in the genome as compared to a TNT-responsive OR gene or that is encoded by a gene that exhibits synteny with a TNT-responsive OR gene and (2) that exhibits greater than 85% protein homology (amino acid identity plus amino acid similarity) as compared to a TNT-responsive OR. Once a TNT-responsive OR has been identified in for example a rat or a mouse, a person skilled in the art can readily identify homologous ORs derived from other species and can verify that they serve the same function. Methods for identifying homologous proteins are well known in the art, see for example Pearson W R. An introduction to sequence similarity ("homology") searching. Curr Protoc Bioinformatics. 2013 June; Chapter 3: Unit3.1, incorporated by reference. Thus the TNT-responsive ORs of the invention include, for example, rat, mouse or other mammalian ORs that are homologs or orthologues to the rat and mouse TNT-responsive ORs identified herein.

A non-exhaustive, non-limiting list of homologs for the TNT-responsive ORs identified in this disclosure can be found in Tables 2 and 4.

As used in this specification, "preferential expression" refers to an increase in the number of cells in a population of cells that express a specific OR as compared to wild-type cell populations. In the case of *Rattus norvegicus* TNT-responsive ORs, the expression of the TNT-responsive ORs is compared to the expression of other *Rattus norvegicus* ORs. In the case of *Mus musculus* TNT-responsive ORs, expression of the TNT-responsive ORs is compared to the expression of other *Mus musculus* ORs. In one embodiment, the percentage of cells in a population of cells that expresses a TNT-responsive OR is between 10 and 90%.

In one embodiment, the techniques described in International Patent Publication WO2017024028, the content of which is hereby incorporated by reference, are used in conjunction with the disclosed odorant receptor coding sequences (SEQ ID NO:19-32) or OR genes encoding the disclosed amino acid sequences (SEQ ID NO:2-15). This publication describes a method for producing genetically modified non-human vertebrates by inserting DNA from a genome of a non-human vertebrate using a vector. The vector (see FIG. 1) has an transgene backbone, at least three sequential repeats of a DNA sequence that is at least 90% homologous with 5'-ACATAACTTTTTAATGAGTCT-3' (SEQ ID NO: 1). In one embodiment, the DNA sequence is 100% homologous with SEQ ID NO: 1. A transcription start site is disposed downstream of the at least three sequence repeats and the insertion occurs within a 10 kb proximity of the transcription start site (TSS). Any one of the disclosed odorant receptor coding sequence is disposed downstream of the repeats. Using the M71 transgene backbone including 485 bp of the M71 promoter upstream of the TSS (FIG. 1), a modular version of the transgenic vector was created such that any number of 21 mer repeats can be shuttled into the NheI site at position −485. The modular version of the transgenic vector is a modified form of the M71 7.5 kb minigene disclosed by Rothman (The Promoter of the mouse odorant receptor gene M71; Mol. Cell. Neurosci. 28, 535-546, 2005) wherein the M71 OR CDS has been replaced with an OR CDS of choice. The transgene backbone refers to the disclosed minigene without the M71 OR CDS.

In some embodiments, the biosensor comprises one or more populations of cells, wherein each population preferentially expresses a different TNT-responsive OR. In some embodiments, the biosensor comprises at least two, at least three, at least four, or at least five distinct populations of cells, wherein each population preferentially expresses a different TNT-responsive OR. In embodiments, the biosensor comprises 1, 2, 3, 4, 5, 6, 7, 8, 9, or 10 cell populations, wherein each population preferentially expresses a different TNT-responsive OR. In embodiments, the TNT-responsive OR is selected from SEQ ID NO: 2 to 15. In a non-limiting example, the biosensor comprises two populations of cells with each population selectively expressing a TNT-responsive OR represented by SEQ ID NO 2 or SEQ ID NO 3, respectively. In another embodiment, the biosensor comprises at least three distinct populations of cells, wherein each population preferentially expresses a different TNT-responsive OR selected from SEQ ID NO: 2 to 15. In a non-limiting example, the biosensor comprises three populations of cells with each population selectively expressing a TNT-responsive OR represented by SEQ ID NO: 2 or SEQ ID NO: 3 or SEQ ID NO: 4, respectively. In another example, the biosensor comprises four populations of cells with each population selectively expressing a TNT-responsive OR represented by SEQ ID NO: 2 or SEQ ID NO: 3 or SEQ ID NO: 4 or SEQ ID NO: 5, respectively.

In some embodiments, the biosensor comprises a eukaryotic cell other than a OSN that expresses a TNT-responsive OR disclosed in the instant specification. In some embodiments, the TNT-responsive OR may be fused with a processing/transport segment that directs the processing and transport of the OR to the cell membrane of the host cell. In some embodiments, the biosensor comprises a eukaryotic cell other than an OSN that expresses the hypervariable segment, which contains at least one TNT binding site, of a TNT-responsive OR described in the instant specification. Methods for the expression of ORs and detection of OR activation in yeast have been described in U.S. Pat. No. 7,223,550 and Patent Application No. PCT/2017/019179, both of which are incorporated herein by reference.

In the olfactory system, millions of hair-like olfactory cilia protrude from the dendrites of the OSNs into the mucus of the MOE that lines the nasal cavity. The ORs present in the membranes of these cilia detect odors through G protein-mediated signaling cascade in which binding of the odor activates type III adenylate cyclase (ACIII) and causes a rapid rise in cAMP levels, which bind to cyclic-nucleotide gated channels that cause influx of $Ca^{2+}$. There is also evidence that olfactory receptors can signal via G-protein activation of phosphoinositidase C, with subsequent production of inositol 1,4,5-triphosphate and 1,2-diacylglycerol second messengers.

Olfactory cilia can be detached from the main olfactory epithelium providing an ex vivo system amenable to monitor OR activation as olfactory signal transduction events are exclusively initiated within these cilia. In embodiments of the invention, the biosensor comprises cilia derived from one or more populations of olfactory sensory neurons, wherein the populations of olfactory sensory neurons each preferentially expresses a TNT-responsive OR. Cilia can be obtained from olfactory epithelial tissue by methods known in the art. Kuhlmann et al., (Molecular & Cellular Proteomics (2014), 13:1828-1843) and Mayer et al., (Proteomics (2009), 9:322-334) provide protocols for isolation of olfactory cilia and those protocols are incorporated herein by reference. Sklar et al. (J. of Biological Chemistry (1986), 261:15538-15543), and Pfeuffer et al. (J. of Biological Chemistry (1989), 264:18803-18807) also provide protocols for isolation of olfactory cilia and those protocols are also incorporated herein by reference. Following isolation, cilia preparations may stored at −80° C. for months without significant loss in activity.

In some embodiments, the activation of TNT-responsive ORs is determined in a biochemical assay. In some embodiments, populations of olfactory sensory neurons that express TNT-responsive ORs are isolated and the activation of the OR is detected ex vivo. In one embodiment, the cilia of the OSNs are further isolated using a deciliation protocol and used for the detection of activation of the TNT-responsive OR.

In some embodiments, the biosensor comprises populations of eukaryotic cells disposed on a solid support. In some embodiments, the biosensor comprises populations of olfactory sensory neurons or cilia derived therefrom that were extracted from a transgenic non-human mammal and subsequently disposed on a solid support. Examples of suitable solid supports include, but are not limited to, silicon, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. In general, the solid support allows optical detection and does not appreciably fluoresce. In one embodiment, the surface of the solid support is modified to contain microwells, i.e. depressions in the surface of the solid support. This may be done as is generally known in the art using a variety of techniques, including, but not limited to, photolithography, stamping techniques, pressing, casting, molding, microetching, electrolytic deposition, chemical or physical vapor deposition employing masks or templates, electrochemical machining, laser machining or ablation, electron beam machining or ablation, and conventional machining. As will be appreciated by those in the art, the technique used will depend on the composition and shape of the solid support. In one embodiment, the interior surfaces of the microwells may be coated with a thin film or passivation layer of biologically compatible material. For example, materials known to support cell growth or adhesion may be used, including, but not limited to, fibronectin, any number of known polymers including collagen, polylysine and other polyamino acids, polyethylene glycol and polystyrene, growth factors, hormones, cytokines, etc. In addition, coatings or films of metals such as a metal such as gold, platinum or palladium may be employed. In an alternative embodiment, an indicator compound, for example, a fluorophore, a chromophore or dye, may be attached to the microwell surface for detecting cellular responses to OR activation. In some embodiments, the biosensor further comprises one or more of an electromagnetic radiation source, a detection element, an optical filter, components to deliver or remove fluids, a collection chamber, a cover plate, an electrode, an integrated circuit, and a hydrogel.

A person skilled in the art will appreciate that the activation of the TNT-responsive OR can be measured in various ways. For instance, activation of a TNT-responsive OR may be detected by monitoring a decrease in ATP levels or an increase in $Ca^{2+}$, GDP, cAMP, inositol 1,4,5-triphosphate and/or 1,2-diacylglycerol levels using conventional methods.

In some embodiments, a marker may be provided to detect the interaction of TNT with a TNT-responsive OR. The use of markers permits the measurement of TNT-responsive OR activation using conventional methods, including the measurement of fluorescence, luminescence, phosphorescence, visible light, radioactivity, colorimetry, X-ray diffraction or absorption, electricity or change in electric potential, or magnetism. In some embodiments, the marker may be a fluorescent dye. Examples of suitable dyes include calcium-sensitive dyes such as fura-2, fluo-3, fluo-4, fluo-5F, indo-1, and Oregon Green BAPTA. The marker may be integrated into the biosensor using, for example, the techniques described in International Patent Publication WO2017024028. Such marker proteins may be co-expressed with the one or more preferentially expressed TNT-responsive ORs. Examples of suitable marker proteins include GECO2.1, GCaMP6, Flamindo, Flamindo2 and Pink Flamindo.

In some embodiments, the TNT-responsive OR is further genetically or chemically modified to allow detection of OR activation by inter- or intra-molecular fluorescence resonance energy transfer (FRET), bioluminescence resonance energy transfer (BRET), or bimolecular fluorescence complementation (BiFC).

This written description uses examples to disclose the invention, including the best mode, and also to enable any person skilled in the art to practice the invention, including making and using any devices or systems and performing any incorporated methods. The patentable scope of the invention is defined by the claims, and may include other examples that, occur to those skilled in the art. Such other examples are, intended to be within the scope of the claims if they have structural elements that do not differ from the literal language of the claims, or if they include equivalent structural elements with insubstantial differences from the literal language of the claims.

EXAMPLES

Example 1. Identification of TNT-Responsive ORs in Rat

The discriminatory power of odorant receptors rivals that of the visual and auditory systems, but the patterns of receptor activation by odorant ligands remains elusive. Resolution of this problem has been hampered by the vast amount of ORs expressed in the mammalian nose (greater than 1200 in rats and mice, about 400 in human) and by the fact that odorant receptors are notoriously hard to express in vitro, making high-throughput ligand profiling screen impossible. For these reasons, less than 10% of all odorant receptors have a known ligand and most odorant receptors remain orphans, meaning that their correspondent ligands are unknown.

Figure 2:
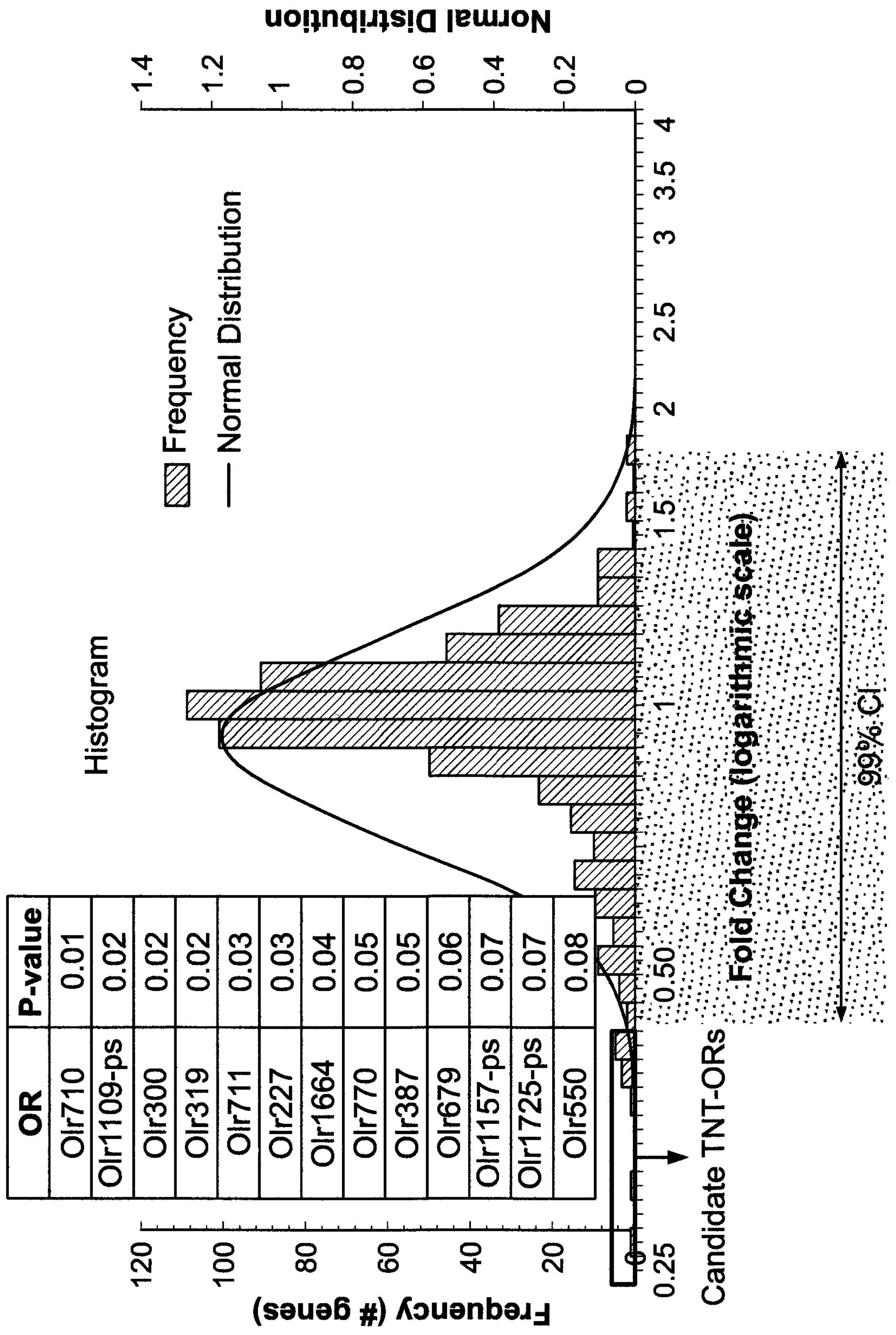
FIG. 2 is a histogram of rat olfactory receptor responses to TNT that identifies candidate receptors.

To identify the odorant receptors that are activated by TNT, a technique called "DREAM" (i.e. Deorphanization of Receptors based on Expression Alterations of mRNA levels) was used, which takes advantage of the generalized reduction in odorant receptor mRNA concentration that occurs after specific OSN activation (von der Weid, B., Rossier, D., Lindup, M., Tuberosa, J., Widmer, A., Col, J. D., Kan, C., Carleton, A., and Rodriguez, I. (2015). Large-scale transcriptional profiling of chemosensory neurons identifies receptor-ligand pairs in vivo. Nat Neurosci 18, 1455-1463; see also US2017/0285009, both encorporated herein by reference). Rats, *Rattus norvegicus*, (n=8 in each group was calculated to be a sufficient sample sin using an alpha of 0.05, a power of 0.95, an effect size d of 1.8 in a one tailed Mann-Whitney U test) were exposed to vehicle control (BLANK) and "breather bags" containing 5% TNT, respectively. Breather bags were obtained from Signature Science, LLC and are commonly used to train Explosive Detection Dogs. After five hours of odor exposure, rats were sacrificed and mRNA was extracted out of the rat olfactory epithelial (OE) tissue using TRIzol® reagent. Subsequent deep sequencing of an olfactory cDNA library corresponding to each animal, allowed calculation of the fold difference in odorant receptor mRNA concentrations between the different groups using a threshold corresponding to genes located outside a 99% confidence interval of a fitted Gaussian distribution. This analysis revealed a list of thirteen rat TNT-responsive ORs (see FIG. 2 and Table 1 for a list of the TNT-responsive OR encoding cDNAs and a list of the corresponding TNT-responsive OR protein sequences). All NCBI Gene ID, as well as NCBI mRNA and protein accession numbers are incorporated herein by reference.

TABLE 1

TNT-responsive ORs identified in *rattus norvegicus*.

| Gene name Rat (*rattus norvegicus*) | Gene location | SEQ ID of corre-sponding protein | NCBI Gene ID | NCBI mRNA Accession No. NCBI Protein Accession No. |
|---|---|---|---|---|
| Olr710 | chr3:74911052-74911997 | SEQ ID NO: 2 | 366113 | NM_001000571.1 NP_001000571.1 |
| Olr1109-ps | chr7:126108561-126109341 | SEQ ID NO: 6 | 405557 | NG_003822.1 NA |
| Olr300 | chr1:193021640-193022564 | SEQ ID NO: 3 | 293599 | NM_001000237.1 NP_001000237.1 |
| Olr319 | chr1:206275703-206276633 | SEQ ID NO: 4 | 309222 | NM_001000506.1 NP_001000506.1 |
| Olr711 | chr3:74921447-74922392 | SEQ ID NO: 7 | 404817 | NM_001000625.1 NP_001000625.1 |
| Olr227 | chr1:158777419-158778373 | SEQ ID NO: 8 | 293370 | NM_001000203.1 NP_001000203.1 |
| Olr1664 | chr17:52755475-52756426 | SEQ ID NO: 9 | 405375 | NM_001001007.1 NP_001001007.1 |
| Olr770 | chr3:97240050-97240989 | SEQ ID NO: 10 | 296023 | NM_001000372.1 NP_001000372.1 |
| Olr387 | chr1:206722468-206723407 | SEQ ID NO: 11 | 292324 | NM_001000109.1 NP_001000109.1 |
| Olr679 | chr3:74335928-74336864 | SEQ ID NO: 12 | 295885 | NM_001000354.1 NP_001000354.1 |
| Olr1157-ps | chr8:18986051-18987018 | SEQ ID NO: 13 | 405170 | NG_003593.1 NA |

TABLE 1-continued

| TNT-responsive ORs identified in *rattus norvegicus*. | | | | |
|---|---|---|---|---|
| Gene name Rat (*rattus norvegicus*) | Gene location | SEQ ID of corre-sponding protein | NCBI Gene ID | NCBI mRNA Accession No. NCBI Protein Accession No. |
| Olr1725-ps | chr20:1848063-1848878 | SEQ ID NO: 14 | 405643 | NG_003912.1 NA |
| Olr550 | chr3:71800992-71814991 | SEQ ID NO: 15 | 295795 | NM_001000322.1 NP_001000322.1 |

Once a TNT-responsive OR is identified, a person skilled in the art can identify homologous or orthologous proteins that fulfill the same function. A non-exhaustive list of homologs and orthologues of rat TNT-responsive ORs based on homology of 85% or more can be found in Table 2 (all NCBI Gene IDs, as well as NCBI mRNA and protein accession numbers are incorporated herein by reference).

same genes. Based on the observed downregulation these genes were identified as genes encoding TNT-responsive ORs. Without wishing to be bound to any particular theory, exposure to TNT is believed to downregulate the expression of these TNT-responsive OR genes.

Additionally, Olr713 and Olr715 (which are paralogs for Olr711) and Olr 297 and Olr303 (which are paralogs for Olr300) are also useful with the disclosed biosensors and methods.

In order to validate the identified TNT-responsive OR genes, the DREAM rat RNA was further analyzed by qPCR. Because odorant receptors are expressed at very low levels, detection of the cDNA is difficult. To overcome this problem, cDNA was preamplified using TAQMAN® PreAmp Master Mix using small amounts of the cDNA without introducing amplification bias into the sample. The qPCR analysis shown in FIG. 4 illustrates the normalized relative Quantities (NRQ) for eight rats in each group (BLANK vs TNT).

TABLE 2

Homologs of rat TNT-responsive ORs identified in this application

| | MOUSE | | | HUMAN | | | CANINE | | |
|---|---|---|---|---|---|---|---|---|---|
| RAT Gene name | Gene name | NCBI Gene ID | NCBI mRNA Accession No. NCBI Protein Accession No. | Gene name | NCBI Gene ID | NCBI mRNA Accession No. NCBI Protein Accession No. | Gene name | NCBI Gene ID | NCBI mRNA Accession No. NCBI Protein Accession No. |
| Olr710 | Olfr1247 | 405093 | NM_001000807.1 NP_001000807.1 | NA | | | NA | | |
| Olr1109-ps | NA | | | NA | | | NA | | |
| Olr300 | Olfr533 | 258056 | NM_001011815.1 NP_001011815.1 | NA | | | NA | | |
| | Olfr530 | 258512 | NM_146519.1 NP_666730.1 | | | | | | |
| Olr319 | Olfr1420 | 258405 | NM_146410.1 NP_666522.1 | OR10V1 | 390201 | NM_001005324.1 NP_001005324.1 | LOC483446 | 483446 | XM_540564.3 XP_540564.3 |
| Olr711 | Olfr1248 | 258405 | NM_146410.1 NP_666522.1 | NA | | | NA | | |
| | Olfr1252 | 404331 | NM_207568.1 NP_997451.1 | NA | | | NA | | |
| | Olfr1250 | 258967 | NM_146965.1 NP_667176.1 | NA | | | NA | | |
| Olr277 | Olfr714 | 259035 | NM_147033.2 NP_667244.2 | OR10A5 | 144124 | NM_178168.1 NP_835462.1 | cOR10A9 | 485353 | XM_848789.3 |
| | | | | OR10A2 | 341276 | NM_001004460.1 NP_001004460.1 | LOC100688800 | 100688800 | XM_003432993.1 XP_003433041.1 |
| | | | | | | | OR4B06 | 485350 | XM_848752.1 XP_853845.1 |
| | | | | | | | OR10B10 | 485354 | XM_542472.3 XP_542472.2 |
| Olr1664 | Olfr1370 | 258578 | NM_146535.1 NP_666746.1 | NA | | | NA | | |
| Olr770 | Olfr1299 | 258886 | NM_146884.2 NP_667095.2 | NA | | | NA | | |
| Olr387 | NA | | | NA | | | NA | | |
| Olr679 | Olfr1222 | 258177 | NM_001011860.1 NP_001011860.1 | NA | | | NA | | |
| Olr1157-ps | NA | | | NA | | | NA | | |
| Olr1725-ps | NA | | | NA | | | NA | | |
| Olr550 | Olfr1107 | 258841 | NM_146844.2 NP_667055.2 | NA | | | LOC483540 | 483540 | XM_540660.3 XP_540660.3 |

Figure 3A:
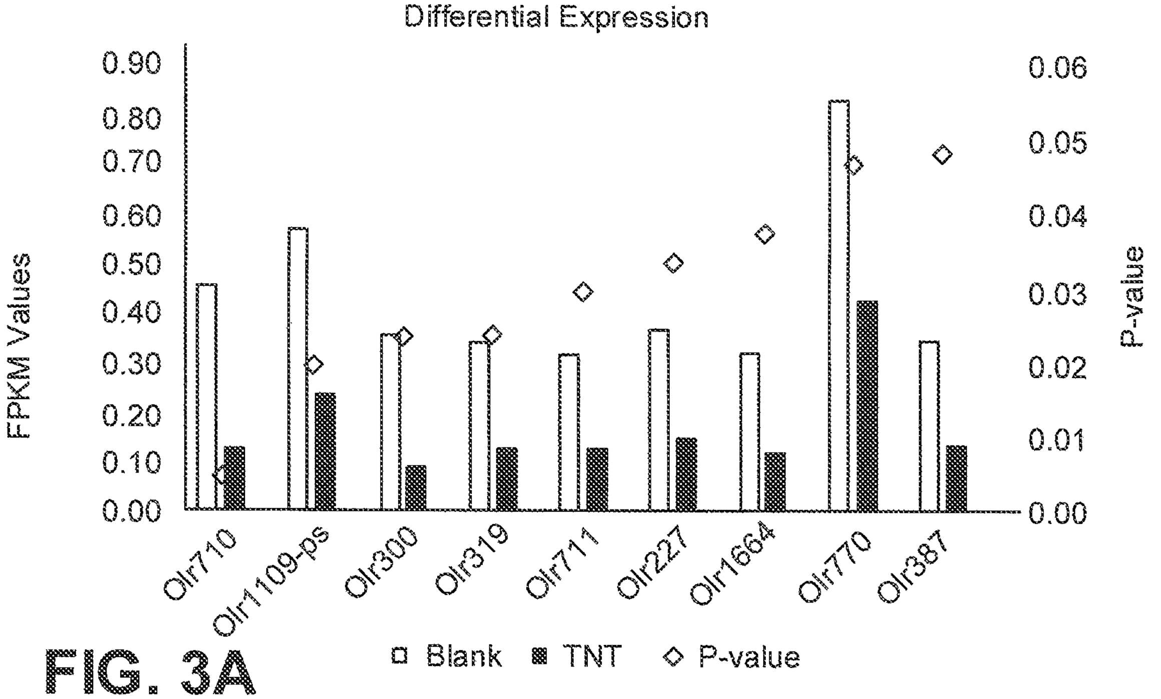
Figure 3B:
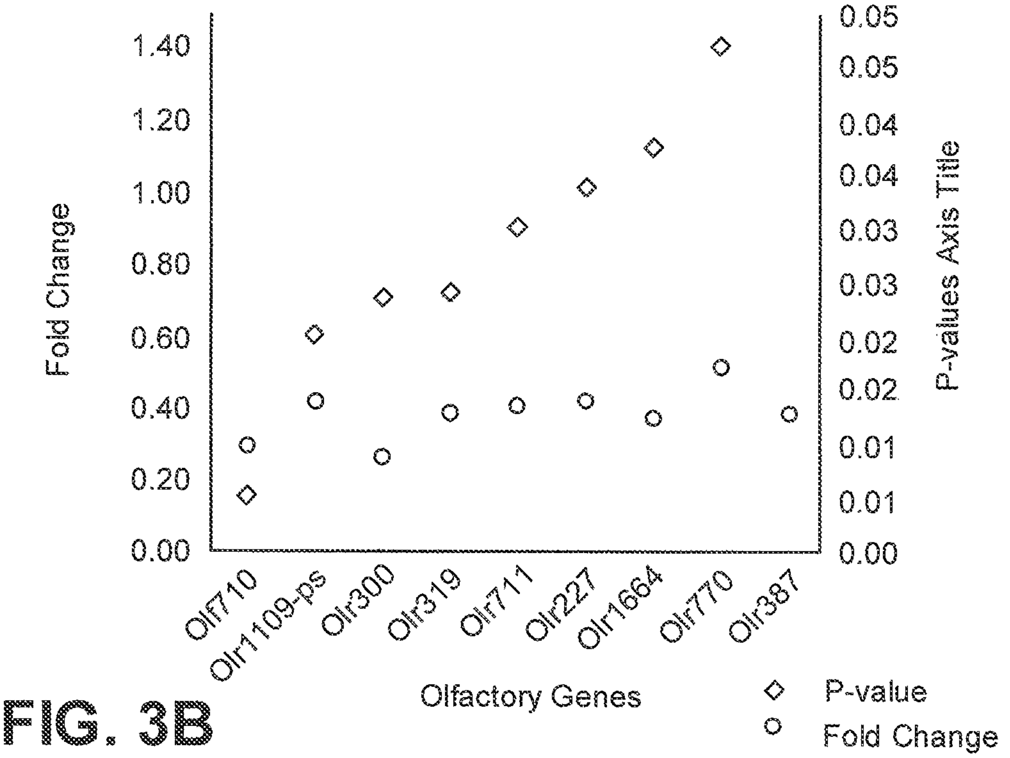
FIG. 3B depicts the fold change for the same.
Figure 4A:
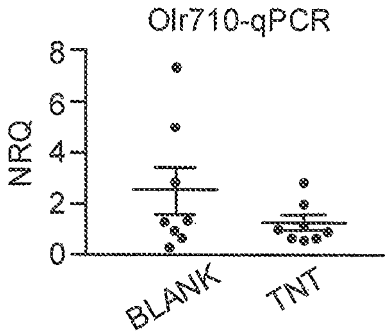
FIGS. 4A to 4E depict graphs that compare Normalized Relative Quantities (NRQ) of cDNAs as obtained by qPCR for both control and TNT groups for three select candidate receptors.
Figure 4B:
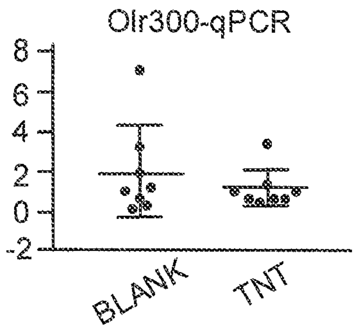
Figure 4C:
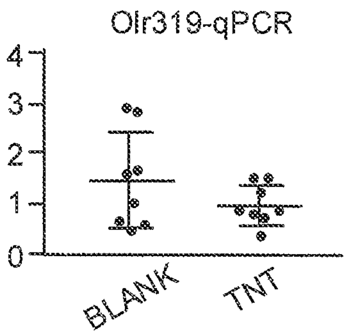
Figure 4D:
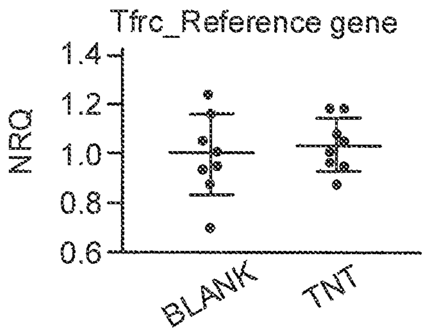
Figure 4E:
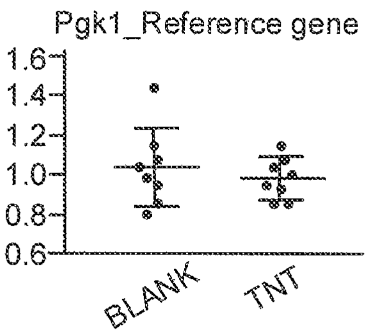

FIG. 3A is a graph depicting Fragments Per Kilobase of transcript per Million reads mapped (FPKM) of both TNT-exposed and BLANK control rats for Olr710, Olr1109-ps, Olr300, Olr319, Olr711, Olr227, Olr1664, Olr770 and Olr387. P-values are also depicted which show the correlations are significant. FIG. 3B depicts the fold change of these Three rat TNT-responsive OR genes (Olr710, Olr300 and Olr319) were detected by qPCR. An unpaired t-test analysis did not reveal statistical differences between BLANK and TNT groups using the qPCR calculated NRQ (Normalized Relative Quantities) values. However, a downregulation trend is visible for the TNT-responsive OR genes (FIG. 4A to FIG. 4C). Further, for the TNT-responsive OR genes, blank samples show most variation, while the TNT data is very tight (see FIG. 4A, FIG. 4B and FIG. 4C). This observation further strengthens the hypothesis that exposure to TNT down regulates the identified TNT-responsive OR genes. As expected, in FIG. 4D and FIG. 4E, no difference is observed in reference gene expression between both groups.

Figure 6:
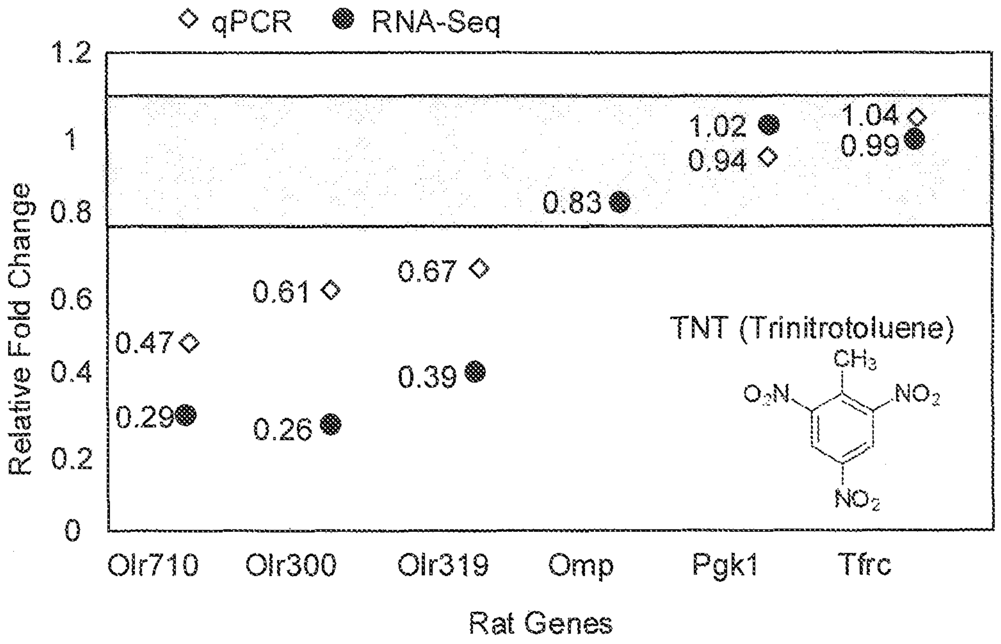
FIG. 6 is a graph showing relative fold difference of gene expression in TNT-treated rats to control groups for Olr710, Olr300 and Olr319 compared to Omp, Pgk1, and Tfrc, which were not differentially expressed. Data obtained from both the transcriptome analysis (circles) as well as the qPCR analysis (diamonds) are compared in this graph. The horizontal grey zone corresponds to values that were not considered to be modulated in response to TNT, such as the reference genes used in this experiment (Pgk1 and Tfrc).
Figure 7:
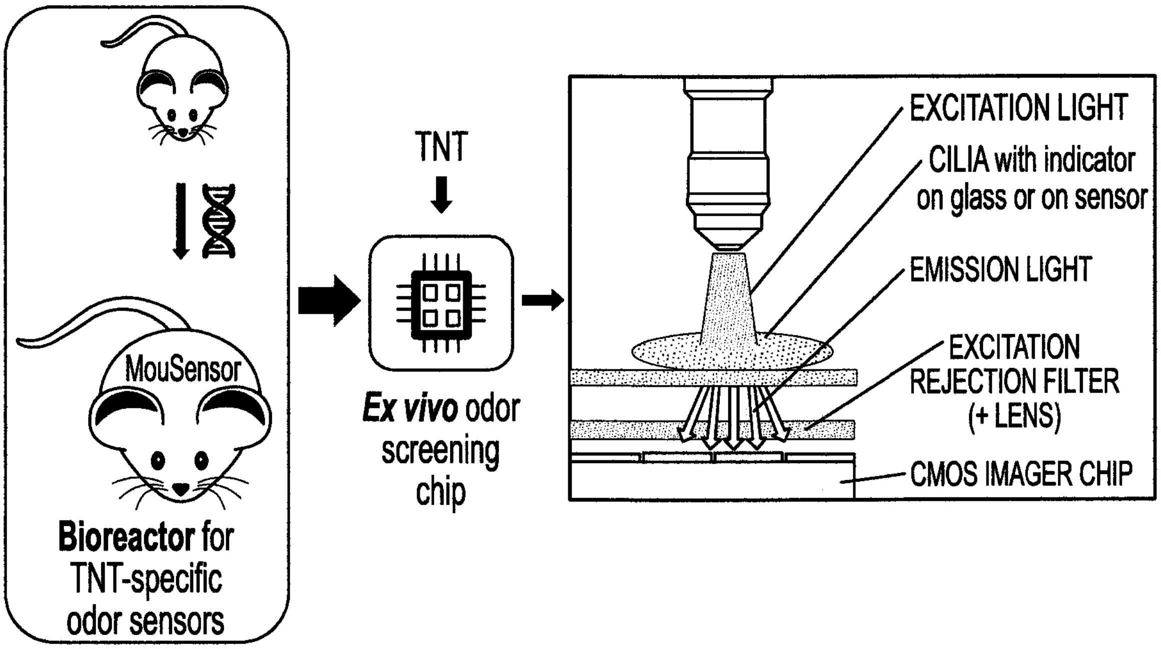
FIG. 7 is a schematic of a method for making a TNT biosensor according to the present invention and detecting TNT. A mammal, here a mouse, is engineered to preferentially express a TNT-responsive OR in its olfactory sensory neurons (OSNs), and the OSNs, or cilia derived therefrom, are obtained and attached to a chip. The chip may contain additional OSNs, or cilia derived therefrom, derived from mice engineered to preferentially express a different OR in its olfactory sensory neurons. Activation of the TNT-responsive ORs, in response to exposure to TNT, is detected using an optical marker.

A comparison between the relative fold changes calculated using both qPCR (diamonds) and RNA-Seq analysis (circles) for the rat TNT-responsive ORs Olr710, Olr300, and Olr319 is shown in FIG. 6. The figure illustrates relative fold difference when comparing TNT-treated rats to Blanks (TNT/Blank). Olfactory transcript levels were determined after five hours of TNT-exposure. The ratio between the values obtained for treated versus non-treated rats are shown. For example: A value of 0.5 means that the target gene is expressed two-fold lower in the TNT-treated group vs the control group. The horizontal grey zone corresponds to values that were not considered to be modulated, such as the reference genes used in this experiment (Omp, Pgk1, and Tfrc). The data demonstrate that the expression of rat TNT-responsive ORs Olr710, Olr300, and Olr319, but not the expression of the control genes, is downregulated upon exposure to TNT.

Example 2. Identification of TNT-Responsive ORs in Mouse

TNT DREAM analysis was also performed on mice (*Mus musculus*, n=7) using the same protocol described above. The mouse TNT-responsive OR genes that were identified are listed in Table 3. A non-exhaustive list of homologs and orthologues of mouse TNT-responsive ORs based on homology of 85% or more can be found in Table 4 (all NCBI Gene IDs, as well as NCBI mRNA and protein accession numbers are incorporated herein by reference).

TABLE 3

Mouse TNT-responsive ORs identified in this application

| Gene name (*Mus musculus*) | NCBI Gene ID | NCBI mRNA Accession No. | NCBI Protein Accession No. | SEQ ID NO: |
|---|---|---|---|---|
| Olfr297 | 258611 | NM_146618.2 | NP_666829.2 | 5 |
| Olfr597 | 258135 | NM_001011845.2 | NP_001011845.2 | 16 |
| Olfr605 | 258156 | NM_001011854.2 | NP_001011854.2 | 17 |
| Olfr566 | 258168 | NM_001011536.1 | NP_001011536.1 | 18 |

TABLE 4

Homologs of mouse TNT-responsive ORs identified in this application

| MOUSE | RAT | | | |
|---|---|---|---|---|
| Gene name | Gene name | NCBI Gene ID | NCBI mRNA Accession No. | NCBI Protein Accession No. |
| Olfr297 | olr30 | 293091 | NM_001000120.1 | NP_001000120.1 |
| Olfr597 | NA | | | |
| Olfr605 | olr95 | 405909 | NM_001001024.1 | NP_001001024.1 |
| Olfr566 | olr77 | 405907 | NM_001001287.1 | NP_001001287.1 |

Figure 5:
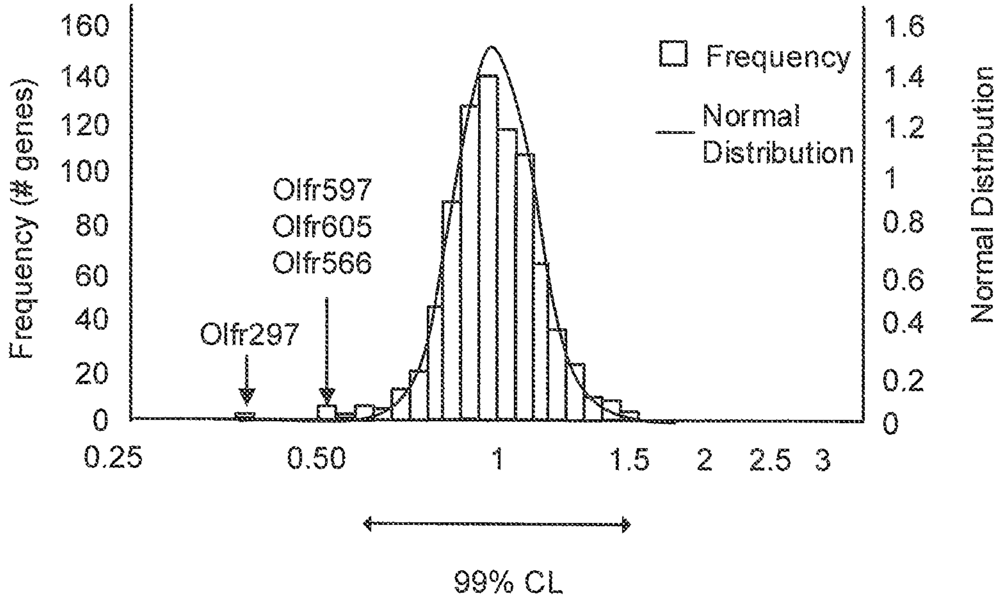
FIG. 5 is a histogram of mouse olfactory receptor responses to TNT that identifies candidate receptors.

FIG. 5 shows mouse TNT-responsive OR genes Olfr297; Olr597 Olfr605 and Olfr566, with Olfr297 (0.37 fold change, 0.03 p-value) being of particular note.

Example 3. Generation of a Transgenic Mouse Preferentially Expressing a TNT-Responsive OR TNT-responsive OR genes are designed with MluI restriction sites flanking the two ends and synthesized as sequence-verified, double-stranded DNA fragments. These DNA fragments are digested with MluI and ligated into the MouSensor vector (~9 kB) (as described in D'Hulst et al. 2016) digested with AscI. Ligated constructs are transformed into DH5alpha *Escherichia coli* cells, and positive clones are grown for plasmid purification. To create constructs expressing different fluorophores (i.e. mVenus, mTeal), the MouSensor-OR constructs are digested with PacI to isolate the OR fragment and ligated into a PacI-digested MouSensor vector containing genes encoding the mVenus or mTeal fluorophores. The final constructs (~10 kB) are digested with PmeI to linearize for pronuclear injection, in which the DNA randomly integrates into the mouse genome. For this, purified DNA is microinjected into a fertilized oocyte, after which the zygote gets reintroduced into a pseudopregnant female mouse (i.e., a female that was mated with a neutered male). The resulting chimeric offspring is subsequently genotyped to verify incorporation of the transgene into the host genome.

Example 4. Isolation of Cilia Derived From Olfactory Sensory Neurons Preferentially Expressing a TNT-Responsive OR The olfactory epithelium from individual 6-8 week old, transgenic mice preferentially expressing a TNT-responsive OR (see Example 3) are dissected and washed briefly in cold buffer containing proteinase inhibitors. The buffer is be replaced with solution containing calcium to "shock" the cilia off of the olfactory neurons [protocol adapted from (Mayer et al. 2009; Kuhlmann et al. 2014), incorporated herein by reference]. Tissue debris is removed by a brief centrifugation step. After two rounds (20 min shock and 10 min centrifugation) of the above shock procedure, the pooled supernatant is spun at high speed in an ultracentrifuge for 30 min. at 4° C. The resulting cilia pellet is resuspended in buffer with 5% glycerol and proteinase inhibitors, aliquoted and flash-frozen by liquid nitrogen. Cilia aliquots are stored at −80° C.

Example 5. Measuring Activation of TNT-Responsive ORs Upon Exposure of the ORs to TNT The assay employed to test activation of TNT-responsive ORs takes advantage of the fact that ORs are G-protein coupled receptors (GPCRs) that couple with adenylate cyclase III. Activated adenylate cyclase produces cyclic AMP (cAMP), which then stimulates protein kinase A (PKA) activity, leading to a decrease in ATP levels. This decrease in ATP is measured using a luciferase reaction, using a commercially available assay, for example, the Promega cAMP-Glo™ Assay. In this assay, which can be adapted for a 384 well format, a lower level of ATP leads to decreased bioluminescence, indicating increased activity of the OR.

100 ng of freshly-thawed cilia isolated from either (1) mice that preferentially express a TNT-responsive OR or (2) wild type mice is placed in triplicate wells and incubated with control (solvent alone) or odor (i.e., TNT) for 15 minutes at 37° C. All subsequent steps are performed as per manufacturer's instructions for the Promega cAMP-Glo™

Assay. Analysis for cilia activation by TNT is performed by calculating the difference in the bioluminescent readout (DRLU) between TNT-treated and untreated cilia for the cilia isolated from either (1) mice that preferentially express a TNT-responsive OR or (2) wild type mice.

For wild type cilia, neither TNT nor the odor control causes activation of the ORs expressed in these cilia, and the ATP levels is about the same upon exposure of these cilia to either the odor control or TNT. As such, the difference in DRLU observed for exposure to the odor control vs to TNT is small.

For cilia isolated from mice that preferentially express a TNT-responsive OR, said TNT-responsive OR is activated upon exposure to TNT, leading to decreased ATP levels as compared to the same cilia exposed to the odor control. Therefore the difference in DRLU observed for exposure to the odor control vs to TNT is significantly greater for these types of cilia.

Viability of the cilia is tested with Forskolin (5 nM). Forskolin (positive control) activates ACIII directly and increases the intracellular cAMP levels.

| Gene | Coding Sequence |
|---|---|
| Olr597 (mouse) | SEQ ID NO: 16 |
| Olf605 (mouse) | SEQ ID NO: 17 |
| Olr566 (mouse) | SEQ ID NO: 18 |
| Olr710 (rat) | SEQ ID NO: 19 |
| Olr300 (rat) | SEQ ID NO: 20 |
| Olr319 (rat) | SEQ ID NO. 21 |
| Olfr297 (mouse) | SEQ ID NO: 22 |
| Olr1109-ps (rat) | SEQ ID NO: 23 |
| Olr711 (rat) | SEQ ID NO: 24 |
| Olr227 (rat) | SEQ ID NO: 25 |
| Olr1664 (rat) | SEQ ID NO: 26 |
| Olr770 (rat) | SEQ ID NO: 27 |
| Olr387 (rat) | SEQ ID NO: 28 |
| Olr679 (rat) | SEQ ID NO: 29 |
| Olr1157-ps (rat) | SEQ ID NO: 30 |
| Olr1725-ps (rat) | SEQ ID NO: 31 |
| Olr550 (rat) | SEQ ID NO: 32 |
| Olr597 (mouse) | SEQ ID NO: 33 |
| Olr605 (mouse) | SEQ ID NO: 34 |
| Olr566 (mouse) | SEQ ID NO: 35 |

What is claimed is:

1. A biosensor for detecting trinitrotoluene (TNT) comprising: one or more populations of olfactory sensory neurons, or cilia derived therefrom, wherein each population of olfactory sensory neurons expresses a polypeptide consisting of the amino acid sequence of SEQ ID NO:2.

2. The biosensor of claim 1, wherein the one or more populations of olfactory sensory neurons, or cilia derived therefrom, are attached to a solid support.

3. The biosensor of claim 2, wherein the solid support is selected from the group consisting of silicon, glass, and polystyrene.

4. The biosensor of claim 1, wherein the biosensor further comprises a marker for detecting activation of the olfactory sensor neurons or cilia, wherein the activation occurs upon exposure of the one or more populations of olfactory sensory neurons, or cilia derived therefrom to a sample comprising TNT.

5. The biosensor of claim 4, wherein the marker comprises one or more calcium-sensitive fluorescent dyes selected from the group consisting of fura-2, fluo-3, fluo-4, fluo-5F, indo-1, and Oregon Green BAPTA.

6. The biosensor of claim 4, wherein the marker is a protein expressed by the one or more populations of olfactory sensory neurons selected from the group consisting of GECO2.1, GCaMP6, Flamindo, Flamindo2, Pink Flamindo.

7. The biosensor of claim 6, wherein the marker is co-expressed with the polypeptide.

8. A method of detecting TNT, the method comprising:

(a) obtaining a sample comprising TNT;

(b) exposing one or more populations of olfactory sensory neurons, or cilia derived therefrom, to the sample, wherein each population of olfactory sensory neurons expresses a polypeptide consisting of the amino acid sequence of SEQ ID NO: 2 and (c) measuring in each of the one or more populations of olfactory sensory neurons, or cilia derived therefrom, the activation of the olfactory sensory neurons or cilia in response to the TNT in the sample.

* * * * *